United States Patent [19]
Mitchell et al.

[11] Patent Number: 5,830,869
[45] Date of Patent: Nov. 3, 1998

[54] THIADIAZOLE AMIDE MMP INHIBITORS

[76] Inventors: Mark Allen Mitchell, 1628 Dover Rd., Kalamazoo, Mich. 49008; Heinrich Josef Schostarez, 3236 Lost Pine Way, Portage, Mich. 49024; Linda Louise Maggiora, 4400 Glenrose Ter., Kalamazoo, Mich. 49008; Thomas J. Lindberg, 2906 W. 1000 North, Michigan City, Ind. 46360

[21] Appl. No.: 878,266

[22] Filed: Jun. 18, 1997

Related U.S. Application Data

[60] Provisional application No. 60/020,188 Jun. 21, 1996.

[51] Int. Cl.$^6$ .................. A61K 31/425; C07C 49/297; C07C 237/14; C07D 285/125
[52] U.S. Cl. .................. 514/19; 514/363; 514/414; 514/415; 514/422; 514/423; 514/563; 514/613; 514/616; 548/139; 548/141; 548/491; 548/523; 564/139; 564/152; 564/155; 564/342; 564/372
[58] Field of Search .................. 514/19, 363, 414, 514/415, 423; 548/139, 141, 491, 523

[56] References Cited

U.S. PATENT DOCUMENTS 5,712,300  1/1998  Jacobsen .................. 514/389

FOREIGN PATENT DOCUMENTS

| | | |
|---|---|---|
| 354881 A | 7/1989 | European Pat. Off. . |
| 396201 A1 | 11/1990 | European Pat. Off. .... C07D 285/135 |
| 0574758A | 12/1993 | European Pat. Off. ...... C07D 209/48 |
| 63-142351 A2 | 6/1988 | Japan . |
| 2282598 | 4/1995 | United Kingdom .......... C07C 235/82 |
| 93/21942 | 11/1993 | WIPO ........................... A61K 37/02 |
| 95/04033-A1 | 2/1995 | WIPO ......................... C07C 259/06 |
| 95/09841 | 4/1995 | WIPO ......................... C07C 323/60 |
| 95/19956 A | 7/1995 | WIPO ......................... C07C 259/06 |
| 96/40745 | 12/1996 | WIPO ............................. C07K 5/062 |
| 97/40031 | 10/1997 | WIPO ........................ C07D 285/125 |

*Primary Examiner*—Johann Richter
*Assistant Examiner*—Jane C. Oswecki
*Attorney, Agent, or Firm*—Lucy X. Yang

[57] ABSTRACT

The present invention provides novel thiadiazole amide derivatives represented by formula I

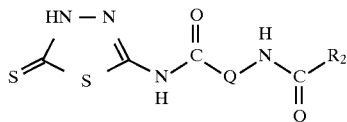

The compounds of the present invention inhibit various enzymes from the matrix metalloproteinase family, predominantly stromelysins, and hence are useful for the treatment of matrix metallo endoproteinase diseases such as osteoarthritis, rheumatoid arthritis, septic arthritis, osteopenias such as osteoporosis, tumor metastasis, periodontitis, gingivitis, corneal ulceration, dermal ulceration, gastric ulceration, inflammation and other diseases related to connective tissue degradation.

28 Claims, No Drawings

THIADIAZOLE AMIDE MMP INHIBITORS

CROSS-REFERENCE TO RELATED APPLICATION

This application claims the benefit of the following provisional application: U.S. Ser. No. 60/020,188, filed Jun. 21, 1996, under 35 USC 119(e)(i).

FIELD OF THE INVENTION

The present invention relates to novel thiadiazole amides or pharmaceutically acceptable salts thereof, and pharmaceutical compositions containing them. Particularly, the present invention relates to the thiadiazole amides having MMP inhibitory activity which are useful in the treatment of diseases related to connective tissue degradation.

BACKGROUND OF THE INVENTION

Loss of connective tissue integrity occurs in many disease processes, including osteoarthritis, rheumatoid arthritis, septic arthritis, osteopenias such as osteoporosis, tumor metastasis (invasion and growth), periodontitis, gingivitis, corneal ulceration, dermal ulceration, gastric ulceration, inflammation and other diseases related to connective tissue degradation. Although there is a high incidence of these diseases in the developed world, there is no treatment that prevents the tissue damage that occurs. Considerable lines of scientific evidence indicate that uncontrolled connective matrix metalloproteinase (MMPs) activity is responsible for the damage, and as a consequence the inhibition of these enzymes has become the target for therapeutic intervention (see Matrisian, L. M., Bases, Vol. 14, pp 445–463 (1992); Emonard, H. et al., Cellular and molecular Biology, Vol. 36, pp 131–153 (1990); Docherty, A. J. P. et al., Annals of the Rheumatic, Vol. 49, pp 469–479 (1990).

The compounds of the present invention inhibit various enzymes from the matrix metalloproteinase family, predominantly stromelysins, and hence are useful for the treatment of matrix metallo endoproteinase diseases such as osteoarthritis, rheumatoid arthritis, septic arthritis, osteopenias such as osteoporosis, tumor metastasis (invasion and growth), periodontitis, gingivitis, corneal ulceration, dermal ulceration, gastric ulceration, inflammation, and other diseases related to connective tissue degradation.

INFORMATION DISCLOSURE

Peptide MMP inhibitors are described in the following:

International Publication No. WO95/09841 discloses new hydroxamic acid derivatives of amino acid amide compounds useful as TNF release and matrix metalloprotease inhibitors, e.g., for treating inflammation, fever or arthritis.

International Publication No. WO95/04033-A1 discloses new succinamide derivatives useful as gelatinase and collagenase inhibitors.

International Publication No. WO93/21942 discloses matrix metallo protease inhibitors for promoting tumour regression by inhibiting cancer cell proliferation and angiogenesis, atherosclerosis, ovarian carcinoma, melanoma and sarcoma.

European Patent Publication 0,574,758A discloses new hydroxamic acid derivatives useful as collagenase inhibitors for the treatment of arthritis, tumors, atherosclerosis, etc.

UK Patent Application GB 2,282,598A discloses hydroxysuccinyl hydroxyamines useful in the prophylaxis or treatment of diseases or conditions mediated by metallo proteinases and/or tumour necrosis factor.

However, compounds in these references bear no structural resemblance to the thiadiazole MMP inhibitors described in the present invention.

The following publications disclose compounds having thiadiazole derivative structure:

International Publication No. WO96/40745 discloses amino acid amides of 5-amino-1,3,4-thiadiazole-2-thione useful as inhibitors of matrix metalloproteiase enzymes.

Abstract of Japanese Patent JP 6,3142,351 A2 discloses thiadiazole derivatives useful in a direct positive color imaging method.

Abstract of European Patent application EP 396201 A1 discloses tautomeric thiadiazoline derivatives useful for the treatment of glaucoma.

Abstract of European Patent application EP 354,881 A discloses 5-acyl:amino-2-sulfonamide-1,3,4-thiadiazole compounds useful as a carbonic anhydrase inhibitors or the treatment of glaucoma.

Derwent abstract 83-750659/35 discloses 2-amino-1,3,4-thiodiazole derivatives useful as antitumour agents.

Co-pending patent application, Ser. No. 60/013,098 discloses novel hydroxamic acid derivatives useful for the treatment of diseases related to connective tissue degradation.

Co-pending U.S. patent application, Ser. No. 60/016,003 discloses novel thiadiazole derivatives useful for the treatment of diseases related to connective tissue degradation.

SUMMARY OF THE INVENTION

The present invention provides novel thiadiazole amides represented by formula I

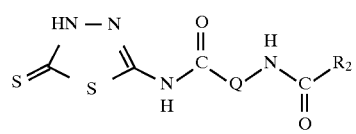

or pharmaceutical acceptable salts thereof wherein:

Q is $\text{---(CHR}_1\text{)}_n\text{---}$, or  a)

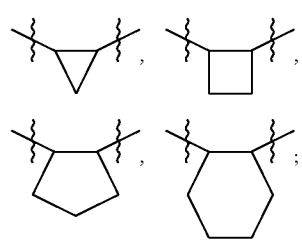
b)

$R_1$ is
a) H,
b) $C_{2-8}$ alkyl,
c) phenyl,
d) $C_{1-8}$ alkyl aryl,
e) —(CH$_2$)$_i$—X—(CH$_2$)$_j$-aryl,
f) —(CH$_2$)$_i$—Het, g) $C_{3-6}$ alkylene,
h) $C_{3-6}$ alkylene aryl,
i) —$(CH_2)_j$-cycloalkyl,
j) —$C(CH_3)_2$—S—$CH_2$—$NHC(=O)R_3$, or
k) —$(CH_2)_i$—$NHC(=O)OR_3$;

$R_2$ is
  a) $C_{1-6}$ alkyl,
  b) —$(CH_2)_j$-aryl,
  c) —$(CH_2)_i$-indol-3-yl,
  d) 9H-fluoren-9-ylmethoxy,
  e) —$(CH_2)_j$—$OR_3$, or

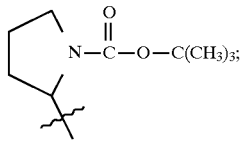
  f)

$R_3$ is
  a) $C_{1-6}$ alkyl, or
  b) —$(CH_2)_j$-aryl;

X is
  a) S, or
  b) O;

aryl is
  phenyl, or benzyl, optionally substituted with one to five of the following:
    a) halogen,
    b) —$NHC(=O)OR_3$,
    c) —$NO_2$, or
    d) —$CF_3$;

Het is
  a 5-, 6-, 9-, or 10-membered heteroaromatic moiety having one or more atoms selected from the group consisting of N, O, and S;

i is 1, 2, 3, or 4;
j is 0, 1, 2, 3, or 4;
n is 1 or 2; and with the following provisos:

a) when n is 1, and $R_1$ is phenylmethoxymethyl, or benzyl, $R_2$ is other than tert-butyoxy, b) when n is 1, $R_1$ is isopropyl, and $R_2$ is tert-butyoxy, the compound is (S) enantiomer, c) when n is 1, $R_1$ is phenylmethyl, and $R_2$ is phenylmethoxy, the compound is (S) enantiomer, d) when n is 1, $R_1$ is indol-3-methyl, and $R_2$ is phenylmethoxy, the compound is (S) enantiomer, or e) when n is 2, at least one $R_1$ is other than hydrogen.

The invention also includes compounds of formula VI

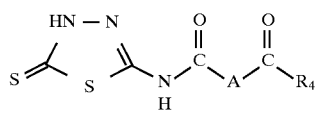 VI or pharmaceutical acceptable salts thereof wherein

A is

 a)

-continued

 b)

and $R_4$ is
  a) —$OCH_2CH_3$,
  b) —$NHCH_3$, or
  c) —$N(CH_2Ph)(OCH_2Ph)$.

The present invention provides novel thiadiazole derivatives useful as preventatives and therapeutics for diseases related to connective tissue degradation.

DETAILED DESCRIPTION OF THE INVENTION

For the purpose of the present invention, the carbon content of various hydrocarbon containing moieties is indicated by a prefix designating the minimum and maximum number of carbon atoms in the moiety, i.e., the prefix $C_{i-j}$ defines the number of carbon atoms present from the integer "i" to the integer "j", inclusive. Thus, $C_{1-4}$ alkyl refers to alkyl of 1–4 carbon atoms, inclusive, or methyl, ethyl, propyl, butyl and isomeric forms thereof.

The term "$C_{1-6}$ alkyl" and "C2-8 alkyl" refer to alkyl groups having one to six or two to eight carbon atoms respectively such as, for example, methyl, ethyl, n-propyl, n-butyl, n-pentyl, n-hexyl, n-heptyl, n-octyl and isomeric forms thereof, and preferably an alkyl group having 4 to 7 carbon atoms.

The term "cycloalkyl" refers to three to six carbon atoms forming cyclopropyl, cyclobutyl, cyclopentyl, cyclohexyl and isomeric forms thereof, and preferably an cycloalkyl group having 5 to 6 carbon atoms.

The term "halogen" refers to fluoro, chloro, bromo, or iodo, preferably fluoro.

The term "$C_{3-6}$ alkylene aryl" refers to any straight or branched alkylene group having three to six carbons attached to an aryl.

The term "Het" refers to a 5-, 6-, 9- or 10-membered heteroaromatic moiety having one or more atoms selected form the group consisting of nitrogen, oxygen, and sulfur forming such groups as, for example, pyridyl, pyrimidinyl, pyridazinyl, 2-indolyl, 3-indolyl, 2-benzimidazole, piperonyl, indazolyl, or quinolyl.

Within the definition of the terms "Het" the nitrogen atom forming the hetero rings may have a protective group such as an acetyl or hydroxyacetyl group.

α-amino acids refer to compounds containing the 2-amino ethanoic acid backbone. Typically these compounds are also further substituted at the 2-position.

β-amino acids refer to compounds containing the 3-amino propanoic acid backbone. Typically these compounds are also further substituted at either or both of the 2 and 3 positions.

The compounds of the present invention can be converted to their salts according to conventional methods.

The term "pharmaceutically acceptable salts" refers to salts useful for administering the compounds of this invention and these include hydrochloride, hydrobromide, hydroiodide, trifluoroacetic acid, sulfate, phosphate, acetate, propionate, lactate, mesylate, maleate, malate, succinate, tartrate, citrate, 2-hydroxyethyl sulfonate, fumarate and the like. These salts may be in hydrated form. Some of the compounds of this invention may form metal salts such as sodium, potassium, calcium and magnesium salts and these are embraced by the term "pharmaceutically acceptable salts".

Certain of the thiadiazole derivatives of the present invention are preferred.

The preferred $R_1$ substituent is hydrogen, phenyl, phenylmethyl, phenylpropyl, (pentafluorophenyl)methyl, n-butyl, isobutyl, sec-butyl, tert-butyl, propyl, isopropyl, 2-methyl-2-butyl, 2-methyl-3-butene-2yl, heptyl, cyclohexyl, cyclohexylmethyl, indol-3-ylmethyl, phenylmethoxy methyl, phenylmethylthiomethyl, 2-[((acetylamido)methyl)thio]-2-propyl, 2-methyl-4-phenyl-2-butyl, 2-methyl-4-phenyl-30 3-buten-2-yl, 2-methyl-5-phenyl-3-penten-2-yl, 2-methyl-5-phenyl-2-pentyl, 4(carbamic acid phenylmethyl ester)phenylmethyl, or 3-(carbamic acid phenylmethyl ester)-1-propyl.

The preferred $R_2$ substituent is phenyl, phenylmethyl, methoxymethyl, phenylmethoxy, 9H-fluoren-9-ylmethoxy, tert-butyoxy, methyl, 1-phenylethyl, 1-phenybutyl, phenylmethoxymethyl, phenoxymethyl, 1-(2,3,4,5,6-pentafluorophenyl)-2-ethyl, 1-[(1,1-dimethylethoxy)carbonyl]-L-prolyl, or 1H-indol-3-ylmethyl.

The preferred structures and absolute configurations of the compounds claimed in the present invention are as represented in formulas IV and V, which are the optically pure enantiomers having the (S)-configuration at the α position and (R)-configuration at the β position according to the Cahn-Ingold-Prelog nomenclature system. The racemic mixtures are useful in the same way and for the same purpose as the (S) or (R) enantiomers; the difference is that more racemic material may be used to produce the same inhibitory effect. Enantiomerically pure compounds can be prepared directly by using the corresponding enantiomerically pure starting material. The optically pure starting material can be obtained by using a chiral HPLC method to provide the corresponding enantiomers as illustrated in Example 50. The designations (R*,S*) and (R*,R*) are used to indicate the relative sterochemistry of two sterocenters to one another. (R*,R*) means that the two sterocenters have like chirality relative to one another. (R*,S*) means that the two sterocenters have unlike chirality relative to one another.

Depending on substituents, the compounds of this invention may exist in geometric, optical and other isomeric forms and this invention embraces any of these isomers or enantiomers.

Particularly preferred compounds of this invention are as follows:
(1) [2-[(4,5-dihydro-5-thioxo-1,3,4-thiadiazol-2-yl)amino]-2-oxo-1-(phenyl)ethyl]carbamic acid, phenylmethyl ester,
(2) (S)-[1-[[(4,5-dihydro-5-thioxo-1,3,4-thiadiazol-2-yl)amino]carbonyl]-3-phenylpropyl]carbamic acid phenylmethyl ester,
(3) [S-(R*,R*)]-[1-[[(4,5-dihydro-5-thioxo-1,3,4-thiadiazol-2-yl)amino]carbonyl]-2-methylbutyl]carbamic acid phenylmethyl ester,
(4) [S-(R*,R*)]-[1-[[(4,5-dihydro-5-thioxo-1,3,4-thiadiazol-2-yl)amino]carbonyl]-2-methylbutyl]carbamic acid 9H-fluoren-9-yl-methyl ester,
(5) [1-[[(4,5-dihydro-5-thioxo-1,3,4-thiadiazol-2-yl)amino]carbonyl]pentyl]carbamic acid phenylmethyl ester,
(6) (S)-[1-[[(4,5-dihydro-5-thioxo-1,3,4-thiadiazol-2-yl)amino]carbonyl]-2,2-dimethylpropyl]carbamic acid phenylmethyl ester,
(7) (S)-[1-[[(4,5-dihydro-5-thioxo-1,3,4-thiadiazol-2-yl)amino]carbonyl]butyl]-carbamic acid phenylmethyl ester,
(8) [2-[(4,5-dihydro-5-thioxo-1,3,4-thiadiazol-2-yl)amino]-2-oxo-1-[(phenylmethoxy)methyl]ethyl]carbamic acid phenylmethyl ester,
(9) [2-[(4,5-dihydro-5-thioxo-1,3,4-thiadiazol-2-yl)amino]-2-oxo-1-[[(phenylmethyl)thio]methyl]ethyl]carbamic acid phenylmethyl ester,
(10) [1-[[(4,5-dihydro-5-thioxo-1,3,4-thiadiazol-2-yl)amino]carbonyl]octyl]carbamic acid phenylmethyl ester,
(11) (S)-[1-(cyclohexylmethyl)-2-[(4,5-dihydro-5-thioxo-1,3,4-thiadiazol-2-yl)amino]2-oxoethyl]carbamic acid phenylmethyl ester,
(12) (S)-[1-(cyclohexyl)-2-[(4,5-dihydro-5-thioxo-1,3,4-thiadiazol-2-yl)amino]-2-oxoethyl]carbamic acid phenylmethyl ester,
(13) α-(acetylamino)-N-(4,5-dihydro-5-thioxo-1,3,4-thiadiazol-2-yl)-benzeneacetamide,
(14) N-[2-[(4,5-dihydro-5-thioxo-1,3,4-thiadiazol-2-yl)amino]-2-oxo-1-phenylethyl]benzenepropanamide,
(15) N-[2-[(4,5-dihydro-5-thioxo-1,3,4-thiadiazol-2-yl)amino]-2-oxo-1-phenylethyl]benzenepentanamide,
(16) N-(4,5-dihydro-5-thioxo-1,3,4-thiadiazol-2-yl)-α-[[(phenylmethoxy)acetyl]amino]benzeneacetamide,
(17) (2-(((acetylamino)methyl)thio)-1-(((4,5-dihydro-5-thioxo-1,3,4-thiadiazol-2-yl)amino)carbonyl)-2-methylpropyl)carbamic acid phenylmethyl ester,
(18) (Z)-(1-(((4,5-dihydro-5-thioxo-1,3,4-thiadiazol-2-yl)amino)carbonyl)-2,2-dimethyl-4-phenyl-3-butenyl)carbamic acid 1,1-dimethylethyl ester,
(19) (1-(((4,5-dihydro-5-thioxo-1,3,4-thiadiazol-2-yl)amino)carbonyl)-2,2-dimethyl-4-phenylbutyl)carbamic acid 1,1-dimethylethyl ester,
(20) (E)-(1-(((4,5-dihydro-5-thioxo-1,3,4-thiadiazol-2-yl)amino)carbonyl)-2,2-dimethyl-5-phenyl-3-pentenyl)carbamic acid 1,1-dimethylethyl ester,
(21) (1-(((4,5-dihydro-5-thioxo-1,3,4-thiadiazol-2-yl)amino)carbonyl)-2,2-dimethyl-5-phenylpentyl)carbamic acid 1,1-dimethylethyl ester,
(22) (1-(((4,5-dihydro-5-thioxo-1,3,4-thiadiazol-2-yl)amino)carbonyl)-2,2-dimethyl-3-butenyl)carbamic acid 1,1-dimethylethyl ester,
(23) (1-(((4,5-dihydro-5-thioxo-1,3,4-thiadiazol-2-yl)amino)carbonyl)-2,2-dimethylbutyl)carbamic acid 1,1-dimethylethyl ester,
(24) [2-[(4,5-dihydro-5-thioxo-1,3,4-thiadiazol-2-yl)amino]-2-oxo-1-phenylethyl]carbamic acid 1,1-dimethylethyl ester,
(25) (S)-[4-[3-[(4,5-dihydro-5-thioxo-1,3,4-thiadiazol-2-yl)amino]-2-[[(1, 1-dimethylethoxy)carbonyl]amino]-3-oxopropyl]phenyl]carbamic acid phenylmethyl ester,
(26) (S)-N-[1-[[(4,5-dihydro-5-thioxo-1,3,4-thiadiazol-2-yl)amino]carbonyl]-2,2-dimethylpropyl]benzenepropanamide,
(27) (S)-N-[1-[[(4,5-dihydro-5-thioxo-1,3,4-thiadiazol-2-yl)amino]carbonyl]-2,2-dimethylpropyl]-2,3,4,5,6-pentafluorobenzenepropanamide,
(28) (S)-[2-[(4,5-dihydro-5-thioxo-1,3,4-thiadiazol-2-yl)amino]-2-oxo-1-[(pentafluorophenyl)methyl]ethyl]carbamic acid 1,1-dimethylethyl ester,
(29) 1-[(1, 1-dimethylethoxy)carbonyl]-L-prolyl-N-(4,5-dihydro-5-thioxo-1,3,4-thiadiazol-2-yl)-3-methyl-L-valinamide,
(30) (S)-α-N-(4,5-dihydro-5-thioxo-1,3,4-thiadiazol-2-yl)-2,3,4,5,6-pentafluoro-[(1-oxo-3-phenylpropyl)amino]benzenepropanamide,
(31) (S)-[1-[[(4,5-dihydro-5-thioxo-1,3,4-thiadiazol-2-yl)amino]carbonyl]-1,4-butanediyl]biscarbamic acid bis (phenylmethyl) ester,

(32) (S)-N-[1-[[(4,5-dihydro-5-thioxo-1,3,4-thiadiazol-2-yl)amino]carbonyl]-2,2-dimethylpropyl)]-1H-indole-3-acetamide,
(33) (S)-[2-[(4,5-dihydro-5-thioxo-1,3,4-thiadiazol-2-yl)amino]-1-(1H-indol-3-yl-methyl)-2-oxoethyl]carbamic acid, phenylmethyl ester,
(34) (S)-[2-[(4,5-dihydro-5-thioxo-1,3,4-thiadiazol-2-yl)amino]-2-oxo-1-(phenylmethyl)ethyl]carbamic acid phenylmethyl ester,
(35) (S)-[1-[[(4,5-dihydro-5-thioxo-1,3,4-thiadiazol-2-yl)amino]carbonyl]-3-methylbutyl]carbamic acid phenylmethyl ester,
(36) (S)-[1-[[(4,5-dihydro-5-thioxo-1,3,4-thiadiazol-2-yl)amino]carbonyl]-2-methylpropyl]carbamic acid phenylmethyl ester,
(37) (S)-[1-[[(4,5-dihydro-5-thioxo-1,3,4-thiadiazol-2-yl)amino]carbonyl]-2,2-dimethylpropyl]carbamic acid 9H-fluoren-9-yl-methyl ester,
(38) [3-[(4,5-dihydro-5-thioxo-1,3,4-thiadiazol-2-yl)amino]-3-oxo-2-phenylpropyl]carbamic acid phenylmethyl ester,
(39) [3-[(4,5-dihydro-5-thioxo-1,3,4-thiadiazol-2-yl)amino]-3-oxo-2-(phenylmethyl)propyl]carbamic acid phenylmethyl ester,
(40) [3-[(4,5-dihydro-5-thioxo-1,3,4-thiadiazol-2-yl)amino]-3-oxo-1-(1,1-dimethylethyl)propyl]carbamic acid phenylmethyl ester,
(41) [3-[(4,5-dihydro-5-thioxo-1,3,4-thiadiazol-2-yl)amino]-3-oxo-1-phenylpropyl]carbamic acid phenylmethyl ester,
(42) β-(benzoylamino)-N-(4,5-dihydro-5-thioxo-1,3,4-thiadiazol-2-yl)benzenepropanamide,
(43) N-(4,5-dihydro-5-thioxo-1,3,4-thiadiazol-2-yl)-β-[(phenylacetyl)amino]benzenepropanamide,
(44) N-(4,5-dihydro-5-thioxo-1,3,4-thiadiazol-2-yl)-β-[(phenyloxyacetyl)amino]benzenepropanamide,
(45) [3-[(4,5-dihydro-5-thioxo-1,3,4-thiadiazol-2-yl)amino]-3-oxo-1-phenylpropyl]carbamic acid 1,1-dimethylethyl ester,
(46) [3-[(4,5-dihydro-5-thioxo-1,3,4-thiadiazol-2-yl)amino]-3-oxo-1-phenylpropyl]carbamic acid 9H-fluoren-9-yl methyl ester,
(47) N-(4,5-dihydro-5-thioxo-1,3,4-thiadiazol-2-yl)-β-[(methoxyacetyl)amino]benzenepropanamide,
(48) N-(4,5-dihydro-5-thioxo-1,3,4-thiadiazol-2-yl)-β-[(phenoxyacetyl)amino]benzenepropanamide,
(49) N-(4,5-dihydro-5-thioxo-1,3,4-thiadiazol-2-yl)-β-[(phenylmethoxyacetyl)amino]benzenepropanamide,
(50) (S)-[3-[(4,5-dihydro-5-thioxo-1,3,4-thiadiazol-2-yl)amino]-3-oxo-1-phenylpropyl]carbamic acid phenylmethyl ester,
(51) (R)-[3-[(4,5-dihydro-5-thioxo-1,3,4-thiadiazol-2-yl)amino]-3-oxo-1-phenylpropyl]carbamic acid phenylmethyl ester,
(52) (1S-cis-)-[2-[[(4,5-dihydro-5-thioxo-1,3,4-thiadiazol-2-yl)amino]carbonyl]cyclohexyl]carbamic acid 9H-fluoren-9-yl-methyl ester,
(53) (S)-[1-[2-[[4,5-dihydro-5-thioxo-1,3,4-thiadiazol-2-yl)]amino]-2-oxoethyl]-3-methylbutyl]carbamic acid phenylmethyl ester,
(54) (R*,S*)-[2-[[(4,5-dihydro-5-thioxo-1,3,4-thiadiazol-2-yl)amino]carbonyl]-1-(2-methylpropyl)-4-pentenyl]carbamic acid phenylmethyl ester, and
(55) (R*,S*)-[1-[2-[(4,5-dihydro-5-thioxo-1,3,4-thiadiazol-2-yl)amino]-2-oxo-1-(phenylmethyl)ethyl]-3-methylbutyl]carbamic acid phenylmethyl.

The compounds represented by the general formula I can be synthesized by the coupling of N-protected α-amino acids 1 or β-amino acids 2 with 5-amino-1,3,4-thiadiazole-2-thiol as outlined in Scheme I. It is preferred to conduct the reaction in the presence of a trialkylamine base and an activating agent such as carbonyl-diimidazole (CDI), benzotriazole-1-yl-oxy-tris-(dimethylamino)-phosphonium hexafluorophosphate (BOP), or dicyclohexylcarbodiimide (DDC) in an appropriate solvent such as anhydrous THF or DMF.

N-protected α-amino acids and β-amino acids are either commercially available or can be prepared from the corresponding amino acids and a commercially available acid chloride using standard Schotten-Baumann procedures well known in the art. Several N-protected α-amino acids are more complex than the other analogues, their preparations are described in further detail in *J. Org. Chem.*, Vol. 47, pp 3933–3941 (1982); *J. Med. Chem.*, Vol. 36, pp 1100–1103 (1993); *J. Am. Chem. Soc.*, Vol. 61, p 2487 (1936); and/or illustrated in Examples. In addition, N-protected β-amino acids can be prepared from the methods outlined in Scheme IIA and Scheme IIB. As shown in Scheme IIA, the β substituted β-amino acid 7 is prepared from a appropriate aldehyde 5 with (carboethoxymethylene)triphenylphosphorane in a suitable solvent such as THF. After purification, the resulting product 6 is heated with ammonia in EtOH to afford 7, which is protected at N-terminal to provide ester 8. Deprotection of C-terminal using TFA/$CH_2Cl_2$ affords the N-protected β substituted β-amino acid 9. As shown in Scheme IIB, N-protected α substituted β-amino acid is prepared by reacting diethyl malonate 10 with N-(chloromethyl)phthalimide in the presence of suitable base such as sodium hydride to afford the phthalimide intermediate 11. Hydrolysis of intermediate 11 followed by protection of N-terminal provides the desired N-protected α substituted β-amino acid.

In a procedure utilizing BOP as an activating agent, after the initial reaction is complete, the crude product is partitioned between organic layer and aqueous layer. The organic layer then is washed by pH 4 buffer. In a procedure utilizing CDI as an activating agent, CDI is usually added to an anhydrous solution of the amino acid around 0° C. The reaction is then brought to room temperature and stirred several hours. Thiadiazole and the base is added and the reaction is allowed to stir at room temperature for several hours to several days. The resulting thiadiazole amides from above mentioned methods are purified by column chromatography (MeOH/$CH_2Cl_2$, or EtOAc/hexane), and/or recrystallization.

The pharmaceutical compositions of this invention may be prepared by combining the compounds of formula I or VI of this invention with a solid or liquid pharmaceutically acceptable carrier, and optionally, with pharmaceutically acceptable adjuvants and excipients employing standard and conventional techniques. Solid form compositions include powders, tablets, dispersible granules, capsules and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water, water-propylene glycol, and water-polyethylene glycol systems, optionally containing conventional coloring agents, flavoring agents, stabilizers and thickening agents.

The pharmaceutical composition is provided by employing conventional techniques. Preferably the composition is in unit dosage form containing an effective amount of the active component, that is, the compounds of formula I or VI according to this invention.

The quantity of active component, that is the compounds of formula I or VI according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

In therapeutic use for treating a patient, suffering from or susceptible to diseases involving connective tissue degradation, or inhibiting various enzymes from the matrix metalloproteinase family, including collagenase, stromelysin, and gelatinase, the compounds or pharmaceutical compositions thereof will be administered orally, parenterally and/or topically at a dosage to obtain and maintain a concentration, that is, an amount or blood-level of active component in the patient undergoing treatment which will be effective to inhibit such enzymes. Generally, an effective amount of the active compound will be in the range of about 0.1 to about 100 mg/kg. It is to be understood that the dosages may vary depending upon the requirements of the patient, the severity of connective tissue degradation being treated, and the particular compounds being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

The compounds of the present invention inhibit various enzymes from the matrix metalloproteinase family, predominantly stromelysins, and hence are useful for the treatment of matrix metallo endoproteinase diseases such as osteoarthritis, rheumatoid arthritis, septic arthritis, osteopenias such as osteoporosis, tumor metastasis (invasion and growth), periodontitis, gingivitis, corneal ulceration, dermal ulceration, gastric ulceration, inflammation and other diseases related to connective tissue degradation. Such diseases and conditions are well known and readily diagnosed by physician of ordinary skill.

Pharmaceutical compositions for parenteral administration will generally contain a pharmaceutically acceptable amount of the compounds according to formula I as a soluble salt (acid addition salt or base salt) dissolved in a pharmaceutically acceptable liquid carrier such as, for example, water-for-injection and a suitably buffered isotonic solution having a pH of about 3.5–6. Suitable buffering agents include, for example, trisodium orthophosphate, sodium bicarbonate, sodium citrate, N-methylglucamine, L(+)-lysine and L(+)-arginine, to name a few. The compounds according to formula I generally will be dissolved in the carrier in an amount sufficient to provide a pharmaceutically acceptable injectable concentration in the range of about 1 mg/ml to about 400 mg/ml. The resulting liquid pharmaceutical composition will be administered so as to obtain the above-mentioned inhibitory effective amount of dosage. The compounds of formula I or VI according to this invention are advantageously administered orally in solid and liquid dosage forms.

Inhibitory activity is evaluated in one or more of the MMP enzymes (stromelysin, gelatinase, and collagenase) in vitro using particle concentration fluorescence assay. An inhibitor binds to MMP enzymes which prevents the degradation of a substrate by stromelysin, gelatinase, or collagenase. The substrate has attached to it a fluorescein and a biotin moiety. The intact substrate then binds to an avidin-coated particle via the biotin moiety. Once the particle is washed and dried, a fluorescent signal is generated since the fluorescent group is attached to the particle. Without an inhibitor present, the substrate is degraded by MMP enzymes and the fluorescein group is removed, therefore, no fluorescent signal can be detected. Testing compounds are dissolved in DMSO to the desired concentration, then the solutions are diluted to 1:5 with MMP buffer (50 mM Tris-HCl, pH 7.5; 150 mM NaCl; 0.02% $NaN_3$). Serial two-fold dilutions of each compound are prepared. A concentrated, activated enzyme solution is transferred into each plate of the testing compounds, and the mixture is incubated at room temperature for 15 minutes. Thawed MMP substrate is then added into all plates, and the plates are incubated in the dark for 1–3 hours at room temperature. At this point, the substrate mixture is mixed with 0.1% avidin-coated polystyrene particles. After 15 minutes, the fluorescence values are measured following filtration and washing of the beads. Ki values are then calculated. Inhibitory data for the compounds of this invention are shown in TABLE 1. Compounds with lower Ki values are expected to be more effective as MMP inhibitors. It is expected that a compound with a Ki less than 15 $\mu$M against stromelysin will display therapeutic effects in connective tissue disorders.

TABLE 1

MMP Inhibition Constants (Ki, $\mu$M) for Thiadiazole Amide Derivatives

| Example No. | Stromelysin Ki ($\mu$M) | Example No. | Stromelysin Ki ($\mu$M) |
| --- | --- | --- | --- |
| 1 | 1.21 | 2 | 13.9 |
| 3 | 1.24 | 4 | 0.95 |
| 5 | 2.42 | 6 | 0.53 |
| 7 | 2.31 | 8 | 8.06 |
| 9 | 9.45 | 10 | 6.32 |
| 11 | 6.1 | 12 | 0.84 |
| 13 | 1.8 | 14 | 0.64 |
| 15 | 1.38 | 16 | 0.38 |
| 17 | 1.77 | 18 | 1.8 |
| 19 | 6.2 | 20 | 3.06 |
| 21 | 2.72 | 22 | 3.51 |
| 23 | 2.14 | 24 | 1.98 |
| 25 | 2.48 | 26 | 0.24 |
| 27 | 0.91 | 28 | 2.22 |
| 29 | 1.47 | 30 | 0.97 |
| 31 | 2.81 | 32 | 0.41 |
| 33 | 10.2 | 34 | 6.09 |
| 35 | 2.22 | 36 | 1.16 |
| 37 | 0.12 | 38 | 2.27 |
| 39 | 1.32 | 40 | 11.1 |
| 41 | 0.40 | 42 | 1.36 |
| 43 | 0.655 | 44 | 0.69 |
| 45 | 0.72 | 46 | 0.44 |
| 47 | 1.36 | 48 | 0.313 |
| 49 | 0.84 | 51 | 1.5 |
| 52 | 0.26 | 53 | 15 |
| 54 | 1.2 | 55 | 1.91 |
| 56 | 1.7 | 57 | 4.05 |
| 58 | 5 | 59 | 4.3 |
| 60 | 10.3 | | |

In order to more fully illustrate the nature of the invention and the manner of practicing the same, the following experimental examples are presented, but they should not be taken as limitations.

Thiadiazole Coupling—General Method A

To a solution of the protected amino acid in freshly distilled THF (0.2M) at 0° C. in a flame-dried flask under nitrogen is added carbonyldiimidazole (CDI) (1.1 molar equivalents). The reaction is allowed to attain ambient temperature. When tlc analysis indicates no remaining starting amino acid (usually 2–3 hours), 5-amino-1,3,4-thiadiazole-2-thione (1.1 equivalents) and a tertiary amine base (either diisopropylethyl amine or triethyl amine, 1.1–2 molar equivalents) are added to the solution. The reaction is allowed to stir for several hours to 10 days, whereupon the solvent is removed in vacuo and the product is partitioned between $CH_2Cl_2$ and aqueous citric acid (1M). The $CH_2Cl_2$ layer is dried over $MgSO_4$ or $NaSO_4$ and concentrated to provide the crude thiadiazole amide, which is purified by chromatography (elution with 0–10% methanol/dichloromethane) and/or recrystallization.

Thiadiazole Coupling—General Method B

The N-protected amino acid (1 equivalent), 5-amino-1,3,4-thiadiazole-2-thione (1 equivalent), and diisopropylethylamine (2 equivalents) are dissolved in dry THF to give a clear solution. Benzotriazole-1-yl-oxy-tris-(dimethylamino) phosphomuim hexafluorophosphate (BOP, 1 equivalent) is then added to the reaction as a solid. The reaction is allowed to stir overnight at room temperature. The solvent is then removed under reduced pressure and the residue is partitioned between ethyl acetate and aqueous potassium bicarbonate. The organic phase is separated and washed with aqueous potassium bicarbonate followed by aqueous citric acid. The organic phase is dried over magnesium sulfate, filtered, and concentrated under reduced pressure to give the crude product. The product is purified by chromatography (elution with 50–70% hexane\EtOAc\2% HOAc, or 10–30% $CH_3OH/CH_2Cl_2$) and\or recrystallization.

Preparation of N-Protected α-Amino Acids

EXAMPLE 1

Preparation of [2-[(4,5-dihydro-5-thioxo-1,3,4-thiadiazol-2-yl)amino]-2-oxo-1-phenylethyl] carbamic acid, phenylmethyl ester

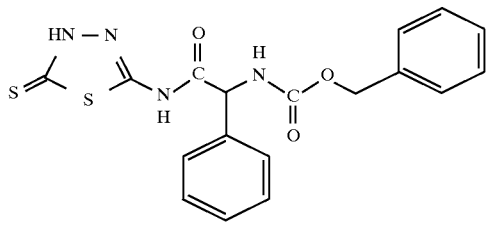

Following the general procedure outlined in method A, and making non critical variations but starting with Cbz-(±)-phenylglycine, the title compound is obtained as a yellow solid.

$^1$H NMR (DMSO-$d_6$) δ 5.07, 5.46, 7.20–7.48, 8.35, 12.85, 14.11;

$^{13}$C NMR (DMSO-$d_6$) ppm 58.1, 65.7, 127.7, 127.8, 128.2, 128.4, 128.6, 135.6, 136.6, 151.7, 155.8, 170.2, 183.6;

IR (mull) 3086, 3030, 2337, 2120, 1946, 1705, 1683, 1578, 1539, 1498, 1308, 1281, 1072, 1054, 695 cm$^{-1}$;

MS (EI) m/z 400 (M+), 382, 292, 148, 108, 107, 106, 91, 79, 77, 51.

EXAMPLE 2

Preparation of (S)-[1-[[(4,5-dihydro-5-thioxo-1,3,4-thiadiazol-2-yl)amino]carbonyl]-3-phenylpropyl] carbamic acid phenylmethyl ester

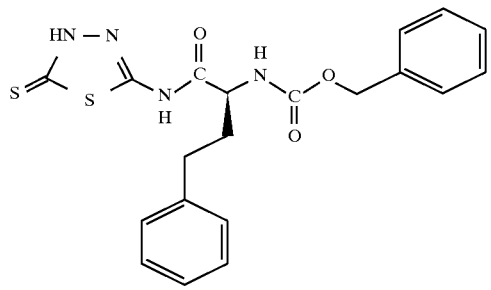

Following the general procedure outlined in method A, and making non critical variations but starting with Cbz-L-homophenylalanine, the title compound is obtained as a white solid.

$^1$H NMR (DMSO-$d_6$) δ 6 1.89, 2.65, 4.23, 5.06, 7.15–7.39, 7.93, 12.63, 14.10;

$^{13}$C NMR (DMSO-$d_6$) ppm 31.5, 32.7, 54.3, 65.6, 125.8, 127.7, 127.8, 128.2, 128.3, 136.7, 140.7, 151.9, 156.0, 172.1, 183.6;

IR (mull) 3332, 2362, 2187, 1950, 1691, 1575, 1525, 1304, 1276, 1268, 1250, 1070, 1048, 750, 700 cm$^{-1}$;

MS (EI) m/z 428 (M+), 428, 224, 223, 134, 133, 117, 92, 91, 76, 65.

EXAMPLE 3

Preparation of [S-(R*,R*)]-[1-[[(4,5-dihydro-5-thioxo-1,3,4-thiadiazol-2-yl)amino]carbonyl]-2-methylbutyl[carbamic acid phenylmethyl ester

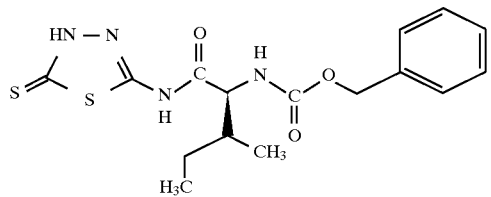

Following the general procedure outlined in method A, and making non critical variations but starting with Cbz-L-isoleucine, the title compound is obtained as a yellow solid. mp 192°–195° C.

$^1$H NMR (DMSO-$d_6$) δ 0.79–0.85, 1.18, 1.44, 1.78, 4.12, 5.03, 7.23–7.37, 7.76, 12.62, 14.11;

$^{13}$C NMR (DMSO-$d_6$) ppm 10.5, 15.1, 24.3, 35.2, 58.8, 65.6, 127.7, 127.8, 128.2, 136.7, 151.6, 156.1, 171.9, 183.5;

IR (mull) 3270, 3204, 3129, 2336, 1948, 1707, 1694, 1684, 1667, 1582, 1341, 1297, 1265, 1074, 1068 cm$^{-1}$;

MS (EI) m/z 380 (M+), 380, 223, 176, 133, 92, 91, 86, 69, 65, 57;

[α]$_D$ (DMSO)=−14°.

EXAMPLE 4

Preparation of [S-(R*,R*)]-[1-[[(4,5-dihydro-5-thioxo-1,3,4-thiadiazol-2-yl)amino]carbonyl]-2-methylbutyl]carbamic acid 9H-fluoren-9-yl-methyl ester

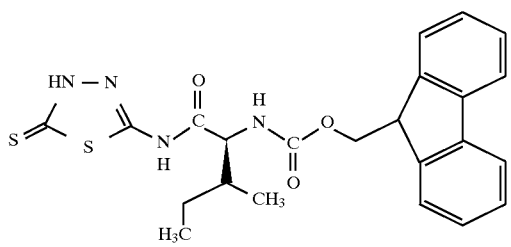

Following the general procedure outlined in method A, and making non critical variations but starting with Fmoc-L-isoleucine, the title compound is obtained as a cream colored foam.

$^1$H NMR (DMSO-d$_6$) δ 0.85, 1.22, 1.49, 1.83, 4.15, 4.24–4.37, 7.33, 7.42, 7.75, 7.88, 12.64, 14.14;

$^{13}$C NMR (DMSO-d$_6$) ppm 10.5, 15.1, 24.4, 35.7, 46.6, 58.8, 65.7, 120.0, 125.2, 127.0, 140.6, 143.7, 151.6, 156.1, 172.0, 183.6;

IR (mull) 3180, 3118, 3068, 2335, 1950, 1911, 1691, 1575, 1522, 1300, 1265, 1231, 1068, 759, 741 cm$^{-1}$;

MS (EI) m/z 468 (M+), 180, 179, 178, 177, 176, 166, 165, 133, 85, 69;

[α]$_D$ (DMSO)=−66°.

EXAMPLE 5

Preparation of [1-[[(4,5-dihydro-5-thioxo-1,3,4-thiadiazol-2-yl)amino]carbonyl]pentyl]carbamic acid phenylmethyl ester

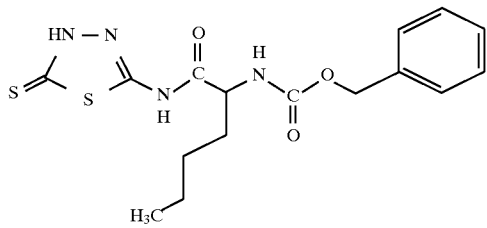

Following the general procedure outlined in method A, and making non critical variations but starting with Cbz-(±)-norleucine, stirred at reflux for 1 day, the title compound is obtained as a yellow solid. mp 169°–171° C.

$^1$H NMR (DMSO-d$_6$) δ 0.85, 8, 1.61, 4.18, 5.03, 7.31, 7.78, 12.60, 14.11;

$^{13}$C NMR (DMSO-d$_6$) ppm 13.7, 21.6, 27.5, 30.7, 54.4, 65.5, 127.7, 127.8, 128.3, 136.7, 151.9, 156.0, 172.4, 183.6;

IR (mull) 3326, 3187, 3091, 3032, 1952, 1689, 1676, 1574, 1540, 1498, 1302, 1261, 1218, 1070, 1049 cm$^{-1}$;

MS (EI) m/z 380 (M+), 380, 248, 223, 176, 133, 92, 91, 86, 69, 65.

EXAMPLE 6

Preparation of (S)-[1-[[(4,5-dihydro-5-thioxo-1,3,4-thiadiazol-2-yl)amino]carbonyl]-2,2-dimethylpropyl] carbamic acid phenylmethyl ester

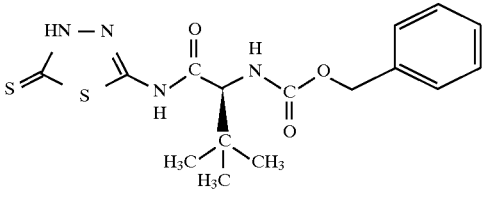

Following the general procedure outlined in method A, and making non critical variations but starting with Cbz-L-tert-leucine, the title compound is obtained as an off-white solid.

$^1$H NMR (DMSO-d$_6$) δ 0.95, 4.17, 5.05, 7.25–7.37, 7.67, 12.6, 14.11;

$^{13}$C NMR (DMSO-d$_6$) ppm 26.2, 33.8, 62.4, 65.6, 127.7, 128.2, 128.4, 128.9, 151.5, 156.2, 170.7, 183.5;

IR (mull) 3191, 3116, 3068, 2336, 1950, 1702, 1669, 1575, 1540, 1498, 1296, 1258, 1213, 1065, 696 cm$^{-1}$;

MS (EI) m/z 380 (M+), 380, 223, 176, 133, 92, 91, 86, 69, 65, 57;

[α]$_D$ (DMSO)=−20°.

EXAMPLE 7

Preparation of (S)-[1-[[(4,5-dihydro-5-thioxo-1,3,4-thiadiazol-2-yl)amino]carbonyl]butyl]carbamic acid phenylmethyl ester

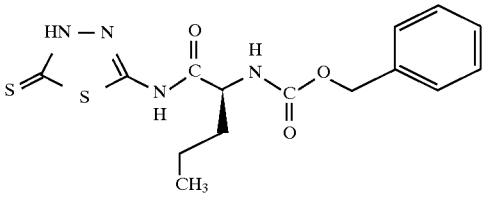

Following the general procedure outlined in method A, and making non critical variations but starting with Cbz-L-norvaline, the title compound is obtained as a white solid.

$^1$H NMR (DMSO-$_6$) δ 0.87, 1.33, 1.61, 4.22, 5.04, 7.36, 7.78, 12.61, 14.11;

$^{13}$C NMR (DMSO-d$_6$) ppm 13.3, 18.6, 33.0, 54.2, 65.6, 127.7, 128.1, 128.3, 136.7, 151.9, 156.0, 172.4, 183.6;

IR (mull) 3308, 3146, 3031, 1954, 1690, 1573, 1533, 1499, 1301, 1263, 1226, 1070, 805, 737, 696 cm$^{-1}$;

MS (EI) m/z 366 (M+), 366, 234, 223, 162, 133, 92, 91, 72, 65, 55;

[α]$_D$ (DMSO)=−32°.

EXAMPLE 8

Preparation of [2-[(4,5-dihydro-5-thioxo-1,3,4-thiadiazol-2-yl)amino]-2-oxo-1-[(phenylmethoxy)methyl]ethyl]carbamic acid phenylmethyl ester

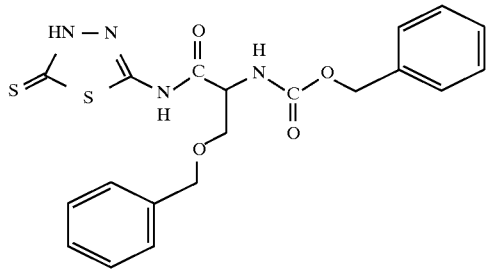

Following the general procedure outlined in method A, and making non critical variations but starting with Cbz-(±)-serine-O-benzyl ether; the title compound is obtained as a white solid.

$^1$H NMR (DMSO-d$_6$) δ 3.67, 4.50, 4.53, 5.04, 7.26–7.36, 7.87, 12.69, 14.13;

$^{13}$C NMR (DMSO-d$_6$) ppm 54.4, 65.7, 68.7, 72.0, 127.3, 127.4, 127.7, 127.8, 128.1, 128.2, 136.6, 137.8, 151.7, 155.9, 170.1, 183.6;

IR (mull) 3354, 2336, 2122, 1988, 1962, 1685, 1571, 1534, 1331, 1313, 1287, 1259, 1097, 1074, 776 cm$^{-1}$;

MS (EI) m/z 228, 148, 108, 107, 91, 79, 77, 65, 51, 50.

EXAMPLE 9

Preparation of [2-[(4,5-dihydro-5-thioxo-1,3,4-thiadiazol-2-yl)amino]-2-oxo-1-[[(phenylmethyl)thio]methyl]ethyl]carbamic acid phenylmethyl ester

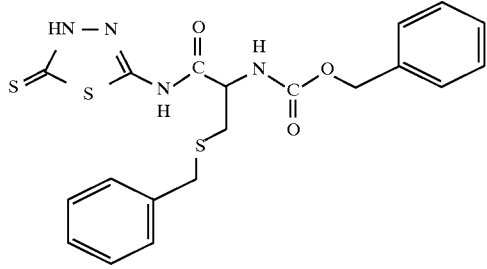

Following the general procedure outlined in method A, and making non critical variations but starting with Cbz-(±)-cysteine-S-benzyl ether, the title compound is obtained as a white solid. mp 134°–136° C.

$^1$H NMR (DMSO-d$_6$) δ 2.64, 2.80, 3.81, 4.51, 5.06, 7.23–7.36, 7.94, 12.81, 14.16;

$^{13}$C NMR (DMSO-d$_6$) ppm 32.2, 35.1, 54.0, 65.7, 126.8, 127.7, 127.8, 128.3, 128.3, 128.8, 136.6, 137.9, 151.7, 155.8, 170.7, 183.6;

IR (mull) 3191, 3026, 2341, 2073, 1944, 1668, 1581, 1534, 1495, 1314, 1269, 1252, 1072, 697, 692 cm$^{-1}$;

MS (EI) m/z 460 (M+), 460, 223, 124, 108, 107, 92, 91, 79, 77, 65.

EXAMPLE 10

Preparation of [1-[[(4,5-dihydro-5-thioxo-1,3,4-thiadiazol-2-yl)amino]carbonyl]octyl]carbamic acid phenylmethyl ester

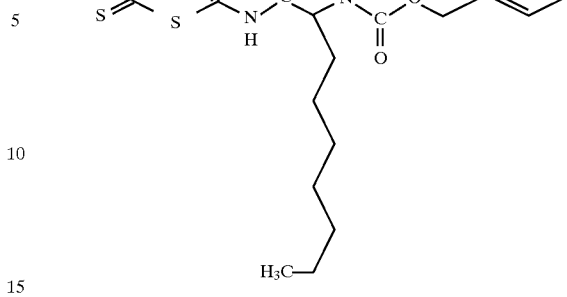

Following the general procedure outlined in method A, and making non critical variations but starting with Cbz-(±)-n-heptylglycine (prepared from 2-aminononanoic acid according to the procedure described in *J. Am. Chem. Soc.*, Vol. 61, p 2487, 1939); the title compound is obtained as a cream foam. mp 162°–163° C.

$^1$H NMR (DMSO-d$_6$) δ 0.82, 1.20, 1.59, 4.17, 5.00, 7.33, 7.72, 12.56, 14.08;

$^{13}$C NMR (DMSO-d$_6$) ppm 14.4, 22.5, 25.8, 28.9, 31.5, 31.6, 55.0, 66.1, 126.3, 128.3, 128.8, 137.3, 152.5, 156.6, 172.9, 184.2;

IR (mull) 3183, 3118, 3067, 3031, 1952, 1686, 1685, 1575, 1526, 1498, 1302, 1267, 1216, 1068, 696 cm$^{-1}$;

MS (EI) m/z 422 (M+), 423, 422, 223, 218, 133, 128, 92, 91, 69, 55.

EXAMPLE 11

Preparation of (S)-[1-(cyclohexylmethyl)-2-[(4,5-dihydro-5-thioxo-1,3,4-thiadiazol-2-yl)amino[-2-oxoethyl] carbamic acid, phenylmethyl ester

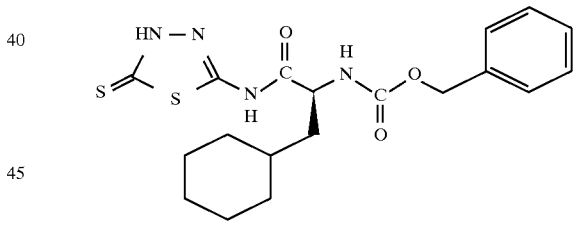

Following the general procedure outlined in method A, and making non critical variations but starting with Cbz-L-cyclohexylalanine the title compound is obtained as an off white foam.

$^1$H NMR (DMSO-d$_6$) δ 0.89, 1.00–1.75, 4.30, 5.04, 7.36, 7.78, 12.67, 14.12;

$^{13}$C NMR (DMSO-d$_6$) ppm 27.2, 27.5, 27.7, 33.1, 34.9, 35.2, 54.0, 67.3, 129.4, 129.6, 130.1, 138.6, 153.8, 157.8, 174.7, 185.4;

IR (mull) 3185, 3122, 2350, 2127, 1952, 1691, 1689, 1575, 1526, 1498, 1305, 1263, 1242, 1067, 1045 cm$^{-1}$;

MS (EI) m/z 420 (M+), 420, 312, 223, 216, 126, 92, 91, 83, 79, 55.

EXAMPLE 12

Preparation of (S)-[1-(cyclohexyl)-2-[(4,5-dihydro-5-thioxo-1,3,4-thiadiazol-2-yl)amino]-2-oxoethyl]carbamic acid phenylmethyl ester Following the general procedure outlined in method A, and making non critical variations but starting with Cbz-L-cyclohexylglycine, the title compound is obtained as a white solid.

$^1$H NMR (DMSO-d$_6$) δ 0.96–1.80, 4.09, 5.02, 7.36, 7.74, 12.6, 14.11;

$^{13}$C NMR (DMSO-d$_6$) ppm 25.3, 25.5, 28.3, 28.8, 59.4, 65.6, 127.7, 128.2, 136.7, 151.6, 156.1, 171.6, 183.5;

IR (mull) 3271, 3219, 3137, 1707, 1695, 1668, 1581, 1498, 1410, 1341, 1298, 1270, 1071, 1060, 697 cm$^{-1}$;

MS (EI) m/z 406 (M+), 388, 298, 250, 148, 112, 108, 107, 91, 79, 77;

[α]$_D$ (DMSO)=+14°.

EXAMPLE 13

Preparation of α-(acetylamino)-N-(4,5-dihydro-5-thioxo-1,3,4-thiadiazol-2-yl)-benzeneacetamide Following the general procedure outlined in method A, and making non critical variations but starting with 2-acetylamino-2-phenylacetic acid, the title compound is obtained as a white solid.

$^1$H NMR (DMSO-d$_6$) δ 1.92, 5.57, 7.30–7.43, 8.80, 12.87, 14.13;

$^{13}$C NMR (DMSO-d$_6$) ppm 23.8, 58.4, 129.6, 130.2, 130.5, 137.6, 154.0, 171.4, 172.0, 185.3;

IR (mull) 3249, 3179, 3047, 2334, 1957, 1678, 1645, 1586, 1535, 1497, 1310, 1291, 1070, 753, 696, cm$^{-1}$;

MS (EI) m/z 308 (M+), 308, 176, 149, 148, 133, 107, 106, 104, 79, 77.

EXAMPLE 14

Preparation of N-[2-[(4,5-dihydro-5-thioxo-1,3,4-thiadiazol-2-yl)amino]-2-oxo-1-phenylethyl]benzenepropanamide Following the general procedure outlined in method A, and making non critical variations but starting with 2-(3-phenylpropanoylamino)-2-phenylacetic acid, the title compound is obtained as a white solid. mp 196°–197.5° C.

$^1$H NMR (DMSO-d$_6$) δ 2.53, 2.82, 5.61, 7.17–7.40, 8.81, 12.89, 14.14;

IR (mull) 3268, 3174, 3105, 3063, 3025, 2346, 1950, 1686, 1641, 1580, 1540, 1497, 1294, 1066, 696, cm$^{-1}$;

MS (EI) m/z 398 (M+), 398, 266, 238, 133, 107, 106, 105, 104, 91, 79.

EXAMPLE 15

Preparation of N-[2-[(4,5-dihydro-5-thioxo-1,3,4-thiadiazol-2-yl)amino]-2-oxo-1-phenylethyl]benzenepentanamide Following the general procedure outlined in method A, and making non critical variations but starting with 2-(5-phenylpentanoylamino)-2-phenylacetic acid, the title compound is obtained as a white solid. mp 210°–211° C. decompose.

$^1$H NMR (DMSO-d$_6$) δ 13.38, 8.69, 7.13–7.39, 5.56, 2.53, 2.22, 1.50;

$^{13}$C NMR (DMSO-d$_6$) ppm 26.5, 32.2, 36.1, 36.6, 58.3, 127.3, 129.6, 129.9, 130.0, 130.2, 130.5, 137.7, 143.9, 154.0, 172.0, 174.3, 185.3;

IR (mull) 3194, 3154, 2346, 2190, 1972, 1952, 1930, 1677, 1637, 1588, 1508, 1497, 1299, 740, 696, cm$^{-1}$;

MS (EI) m/z (rel. intensity) 426 (M+), 426, 294, 266, 133, 117, 107, 106, 104, 91, 79.

EXAMPLE 16

Preparation of N-(4,5-dihydro-5-thioxo-1,3,4-thiadiazol-2-yl)-α-[[(phenylmethoxy)acetyl]amino]benzeneacetamide

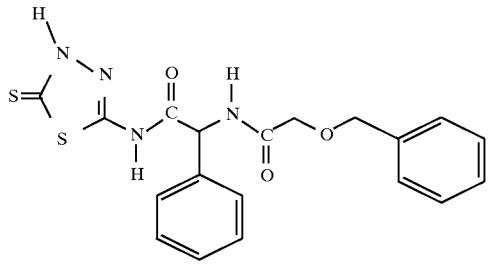

Step 1

Preparation of α-[[(phenylmethoxy)acetyl]amino]benzeneacetic acid

Benzyloxyacetyl chloride (6.3 mL, 40 mmol) is added to a solution of DL-phenylglycine (3.00 g, 19.8 mmol) and NaOH (2.32 g, 58.0 mmol) in 100 mL $H_2O$ and allowed to stir overnight. The reaction pH is adjusted to 11 with 3M NaOH 5 and washed with (3×50 mL) $Et_2O$, then brought to pH=3 with concentrated HCl. The resulting precipitate is collected, washed with $H_2O$ and dried to obtain the title compound as an off-white solid. mp 127°–30° C.

$^1$H NMR (DMSO) δ 4.01, 4.56, 5.39, 7.33–7.38, 8.34;

IR (mull) 3392, 1736, 1717, 1646, 1537, 1341, 1243, 1216, 1190, 1126, 737, 725, 704, 697, 618 $cm^{-1}$;

MS (EI) m/z 299 (M+) 193, 175, 135, 107, 106, 104, 92, 91, 79, 65.

Step 2

Preparation of N-(4,5-dihydro-5-thioxo-1,3,4-thiadiazol-2-yl)-α-[[(phenylmethoxy)acetyl]amino]benzeneacetamide Following the general procedure outlined in method A, and making non critical variations but starting with the product of Step 1, the title compound is obtained as a white solid. mp 96°–100° C.

$^1$H NMR (DMSO) δ 4.01, 4.53, 5.63, 7.26–7.42, 8.49, 12.86, 14.10;

$^{13}$C NMR (DMSO) ppm 56.48, 69.12, 72.87, 128.17, 128.29, 128.78, 129.02, 129.29, 136.44, 138.17, 152.28, 169.65, 170.25, 184.25;

IR (mull) 3101, 3090, 3065, 3030, 1640, 1585, 1530, 1497, 1308, 1100, 1072, 765, 754, 699, 602 $cm^{-1}$;

MS (EI) m/z 414 (M+) 414, 282, 254, 196, 133, 106, 104, 92, 91, 77.

EXAMPLE 17

Preparation of (2-(((acetylamino)methyl)thio)-1-(((4,5-dihydro-5--thioxo-1,3,4-thiadiazol-2-yl)amino)carbonyl)-2-methylpropyl)carbamic acid phenylmethyl ester

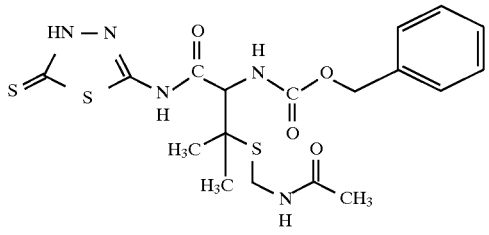

Following the general procedure outlined in method B, and making non critical variations but starting with N-CBZ-S-acetylamino-penicillamine, the title compound is obtained.

$^1$H NMR ($d_6$-DMSO) δ 1.29, 1.33, 1.78, 4.25–4.27, 4.5-4.54, 5.0, 7.25,–7.4, 7.7–7.8, 8.2–8.3, 12.6, 14.1;

MS (FAB) m/z 470 (M+H), 547, 546, 475, 472, 471, 470, 399, 91, 72, 30.

EXAMPLE 18

Preparation of (Z)-(1-(((4,5-dihydro-5-thioxo-1,3,4-thiadiazol-2-yl)amino)carbonyl)-2,2-dimethyl-4-phenyl-3-butenyl)carbamic acid 1,1-dimethylethyl ester

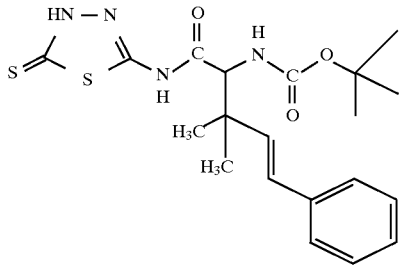

Step 1

Preparation of BOC glycine-1-phenyl-3-methyl 2-butene-3-yl ester

BOC Glycine (1 equivalent), α-(2-methyl-1-propenyl)benzenemethanol (1 equivalent), and DMAP (0.1 equivalent) are placed in a 3-neck flask and dissolved in dry THF. DCC (1 equivalent) is added as a solution in dry THF. A precipitate of dicyclohexylurea quickly forms. The reaction is allowed to stir overnight at room temperature. The reaction mixture is then filtered off and washed with several portions of hexane. The filtrate is concentrated under reduced pressure and the residue is partitioned between ethyl acetate and water. The organic phase is separated and washed with aq potassium bicarbonate, aq 1N HCl, and finally brine. The organic phase is separated, dried (MgSO4), filtered, and concentrated under reduced pressure to give the crude ester, which is purified by chromatography using a gradient of 10% to 20% ethyl acetate/hexane to give the title compound.

Step 2

Preparation of 2-t-butoxycarbonylamino-3,3-dimethyl-5-phenyl-4-pentenoic acid

Hexamethyldisilazane (2.5 equivalents) is dissolved in dry THF and cooled to −78° C. with a dry ice/acetone bath.

N-butyllithium (2.2 equivs, 1.6M in hexanes) is added dropwise via syringe. The solution of LiHMDS is allowed to stir at −78° C. for 10 minutes. The BOC Glycine ester, prepared in Step 1 (1 equivalent) is then added at −78° C. as a solution in dry THF. The solution is allowed to stir at −78° C. for 1 hour and then quenched at −78° C. by the addition of TMSCl (2.2 equivalents, 1M in THF). The reaction is allowed to stir at −78° C. for 1 hour and then allowed to slowly warm to room temperature and stirred overnight. The reaction is quenched with 1N HCl and the solvents are removed under reduced pressure. The residue is partitioned between ethyl acetate and 1N HCl. The organic phase is separated and washed with brine. The organic phase is dried and concentrated under reduced pressure to give the title compound which is then purified via reverse phase chromatography using a gradient from 30% acetonitrile to 70% acetonitrile/water (0.1% TFA added to both the acetonitrile and water).

Step 3

Preparation of (Z)-(1-(((4,5-dihydro-5-thioxo-1,3,4-thiadiazol-2-yl)amino)carbonyl)-2,2-dimethyl-4-phenyl-3-butenyl)carbamic acid 1,1-dimethylethyl ester Following the general procedure outlined in method B and making non critical variations but starting with the product of Step 2, the title compound is obtained.

$^1$H NMR (d$_6$-DMSO) δ 1.21, 1.30, 1.49, 1.63, 3.8–4.05, 4.45–4.6, 5.2–5.3, 5.45–5.55, 6.95–7.3, 12.4, 13.9;

MS (FAB) m/z 435 (M+H), 512, 511, 455, 435, 379, 335, 174, 145, 134, 57.

EXAMPLE 19

Preparation of (1-(((4,5-dihydro-5-thioxo-1,3,4-thiadiazol-2-yl)amino)carbonyl)-2,2-dimethyl-4-phenylbutyl)carbamic acid 1,1-dimethylethyl ester

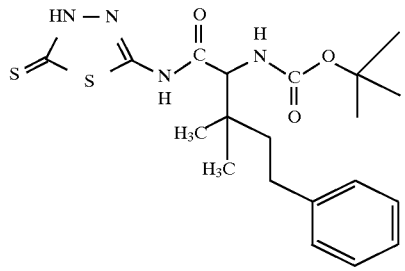

Step 1

Preparation of 2-t-butoxycarbonylamino-3,3-dimethyl-5-phenylpentanoic acid

The product of Example 18, Step 2, and 10% Pd/C are placed in a Parr bottle and mixed with ethyl acetate. The flask is purged with nitrogen and hydrogen and finally pressurized to 35 psi H$_2$. The hydrogenation is run for 4 hours at room temperature. The catalyst is filtered off using a Celite pad and the filtrate is concentrated to give the pure product.

Step 2

Preparation of (1-(((4,5-dihydro-5-thioxo-1,3,4-thiadiazol-2-yl)amino)carbonyl)-2,2-dimethyl-4-phenylbutyl)carbamic acid 1,1-dimethylethyl ester Following the general procedure outlined in method B, and making non critical variations but starting with the product of Step 1, the title compound is obtained.

$^1$H NMR (d$_6$-DMSO) δ 0.71–0.75, 1.05–1.5, 2.95–3.1, 4.25–4.45, 7.05–7.3, 12.1, 13.8;

MS (FAB) m/z 437 (M+H), 513, 457, 437, 381, 337, 176, 134, 91, 57, 41.

EXAMPLE 20

Preparation of (E)-(1-(((4,5-dihydro-5-thioxo-1,3,4-thiadiazol-2-yl)amino)carbonyl)-2,2-dimethyl-5-phenyl-3-pentenyl)carbamic acid 1,1-dimethylethyl ester

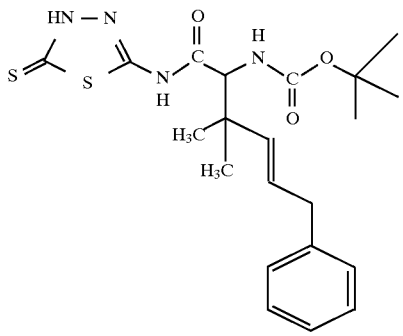

Following the procedures in Example 18, Steps 1–3 and making non critical variations but starting with α-(2-methyl-1-propenyl)benzene ethanol, the title compound is obtained.

$^1$H NMR (d$_6$-DMSO) δ 1.0, 1.35, 3.2–3.5, 4.15–4.3, 5.35–5.5, 5.6–5.7, 6.65–6.75, 7.03, 7.18, 12.4, 14.0;

MS (FAB) m/z 449 (M+H), 526, 525, 449, 393, 349, 188, 134, 91, 57, 41.

EXAMPLE 21

Preparation of (1-(((4,5-dihydro-5-thioxo-1,3,4-thiadiazol-2-yl)amino)carbonyl)-2,2-dimethyl-5-phenylpentyl)carbamic acid 1,1-dimethylethyl ester

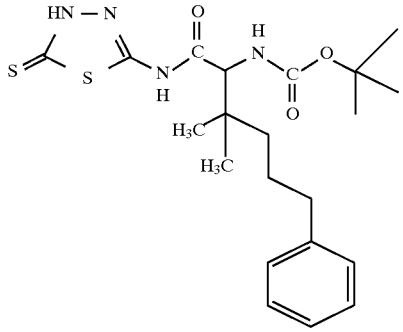

Following the procedures in Example 19, Steps 1 and 2, and making non critical variations but starting with α-(2-methyl-1-propenyl)benzene ethanol, the title compound is obtained.

$^1$H NMR (MHz, d$_6$-DMSO) δ 0.85, 1.1–1.6, 2.4–2.55, 4.15–4.3, 6.75–6.85, 7.1–7.22, 12.4, 14.0;

MS (FAB) m/z 451 (M+H), 528, 527, 451, 395, 351, 234, 190, 134, 91, 57.

EXAMPLE 22

Preparation of (1-(((4,5-dihydro-5-thioxo-1,3,4-thiadiazol-2-yl)amino)carbonyl)-2,2-dimethyl-3-butenyl)carbamic acid 1,1-dimethylethyl ester

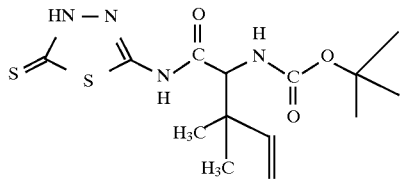

Following the general procedure outlined in method B, and making non critical variations but starting with 2-t-butoxycarbonylamino-3,3-dimethyl-4-pentenoic acid (prepared according to the procedure described in *J. Org. Chem.,* Vol. 47, pp 3933–3941 (1982)), the title compound is obtained.

$^1$H NMR ($d_6$-DMSO) δ 1.0, 1.35, 4.15–4.25, 4.92–4.98, 5.83–5.92, 6.7–6.8;

MS (FAB) m/z 359 (M+H), 511, 467, 437, 436, 435, 359, 144, 142, 98, 57.

EXAMPLE 23

Preparation of (1-(((4,5-dihydro-5-thioxo-1,3,4-thiadiazol-2-yl)amino)carbonyl)-2,2-dimethylbutyl) carbamic acid 1,1-dimethylethyl ester

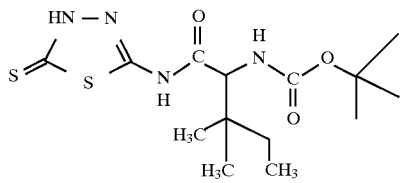

Following the general procedure outlined in method B, and making non critical variations but starting with 2-t-butoxycarbonylamino-3,3-dimethyl-pentanoic acid (prepared according to the procedure described in *J. Org. Chem.,* Vol. 47, pp 3933–3941 (1982) as an unsaturated BOC-amino acid), the title compound is obtained.

$^1$H NMR ($d_6$-DMSO) δ 0.74–0.79, 0.84, 1.1–1.4, 4.14, 6.76, 12.4, 14.0;

MS (FAB) m/z 361 (M+H), 513, 469, 438, 437, 361, 305, 144, 134, 100, 57.

EXAMPLE 24

Preparation of [2-[(4,5-dihydro-5-thioxo-1,3,4-thiadiazol-2-yl)amino]-2-oxo-1-phenylethyl] carbamic acid 1,1-dimethylethyl ester

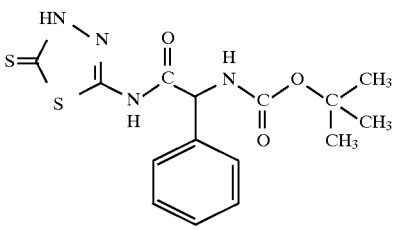

Following the general procedure outlined in method A, and making non critical variations but starting with Boc-(±)-phenylglycine, the title compound is obtained as a white solid. mp 194°–5° C. decompose.

$^1$H NMR (DMSO) δ 1.18, 5.18, 7.10–7.26, 7.61, 12.59, 13.91;

$^{13}$C NMR (DMSO) ppm 28.19, 57.90, 78.81, 127.94, 128.42, 128.66, 136.06, 151.92, 155.26, 170.57, 183.75;

IR (mull) 3325, 3260, 1697, 1679, 1585, 1479, 1445, 1393, 1322, 1308, 1176, 1077, 693, 629, 618 cm$^{-1}$;

MS (EI) m/z 366 (M+) 366, 310, 150, 135, 133, 106, 104, 79, 77, 57.

EXAMPLE 25

Preparation of (S)-[4-[3-[(4,5-dihydro-5-thioxo-1,3,4-thiadiazol-2-yl)amino]-2-[[(1,1-dimethylethoxy)carbonyl]amino]-3-oxopropyl]phenyl]carbamic acid phenylmethyl ester

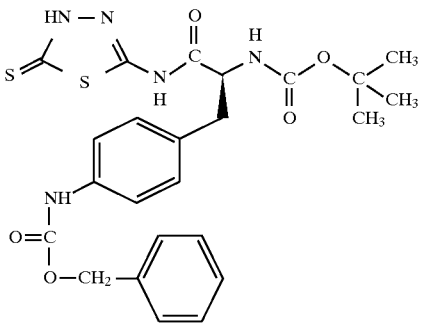

Following the general procedure outlined in method B, and making non critical variations but starting with di-N-benzyloxycarbonyl-4-amino-L-phenylalanine, the title compound is prepared.

$^1$H NMR (DMSO) δ: 1.20–1.29, 2.7, 2.8, 4.3, 5.12, 7.16–7.19, 7.26–7.41, 9.6, 12.6, 14.1.

$^{13}$C NMR (DMSO) ppm: 28.58, 60.23, 66.14, 78.93, 118.48, 128.49, 128.54, 128.91, 130.01, 137.25, 138.03, 152.45, 153.83, 172.64, 184.14.

MS (FAB) m/z: 530, 474, 430, 269, 240, 106, 91, 57.

EXAMPLE 26

Preparation of (S)-N-[1-[[(4,5-dihydro-5-thioxo-1,3,4-thiadiazol-2-yl)amino]carbonyl]-2,2-dimethylpropyl]benzenpropanamide

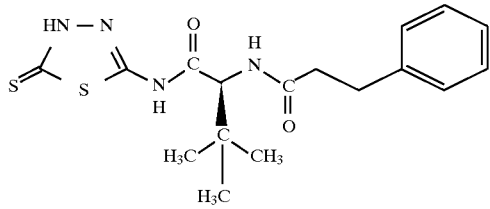

Following the general procedure outlined in method B, and making non critical variations but starting with N-Boc-L-t-leucine, the title compound is obtained.

$^1$H NMR (DMSO) δ: 0.86, 2.48–2.57, 2.75–2.80, 4.39–4.42, 7.12–7.22, 8.05–8.07, 12.6, 14.1.

MS(EI): at m/z 378, 246, 318, 160, 149, 133, 105, 91, 86.

EXAMPLE 27

Preparation of (S)-N-[1-[[(4,5-dihydro-5-thioxo-1,3,4-thiadiazol-2-yl)amino]carbonyl]-2,2-dimethylpropyl]-2,3,4,5,6-pentafluorobenzenepropanamide

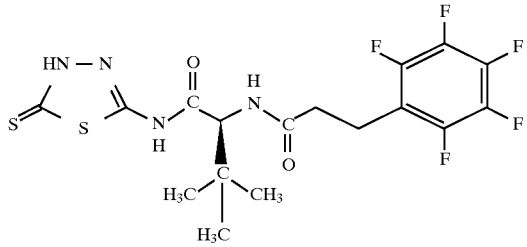

Step 1

Preparation of dihydropentafluorocinnamic acid 1.0 Gram of pentafluorocinnamic acid, 50 mg of 10% Pd/C and 50 mL of EtOH are hydrogenated in a Parr bottle at 30 psi of hydrogen for 3 hours. The catalyst and solvent are removed to give the title compound.

Step 2

Preparation of (S)-N-[1-[[(4,5-dihydro-5-thioxo-1,3,4-thiadiazol-2-yl)amino]carbonyl]-2,2-dimethylpropyl]-2,3,4,5,6-pentafluorobenzenepropanamide Following the general procedure outlined in method B, and making non critical variations but starting with the product of Step 1, the title compound is obtained.

$^1$H NMR (DMSO) δ: 0.86, 2.52–2.54, 2.86–2.88, 4.34–4.37, 8.1–8.12, 12.5, 14.1.

MS(EI): m/z: 468, 336, 308, 195, 181, 133, 86.

EXAMPLE 28

Preparation of (S)-[2-[(4,5-dihydro-5-thioxo-1,3,4-thiadiazol-2-yl)amino]-2-oxo-1-[(pentafluorophenyl)methyl]ethyl]carbamic acid 1,1-dimethylethyl ester

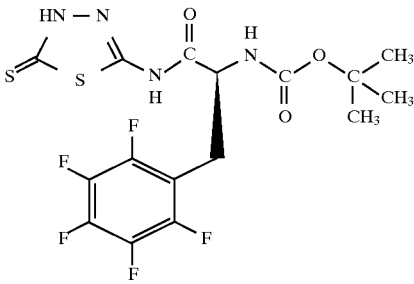

Following the general procedure outlined in method B, and making non critical variations but starting with N-Boc-pentafluoro-L-phenylalanine, the title compound is obtained.

$^1$H NMR (DMSO) δ: 1.29, 3.02–3.10, 4.41–4.43, 7.37–7.39, 12.6, 14.1.

MS(EI): m/z: 470, 414, 397, 370, 210, 133, 57.

EXAMPLE 29

Preparation of 1-[(1,1-dimethylethoxy)carbonyl]-L-prolyl-N-(4,5-dihydro-5-thioxo-1,3,4-thiadiazol-2-yl)-3-methyl-L-valinamide

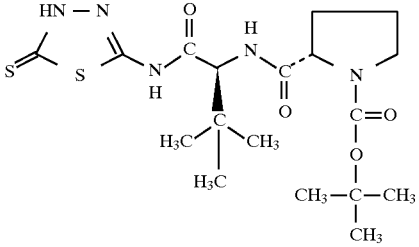

Following the general procedure outlined in method B, and making non critical variations but starting with N-Boc-L-proline, the title compound is obtained.

$^1$H NMR (DMSO)δ: 0.93, 1.3, 1.70, 3.3, 4.27–4.38, 7.93.

MS(EI): m/z: 470, 414, 398, 370, 210, 133, 57.

EXAMPLE 30

Preparation of (S)-α-N-(4,5-dihydro-5-thioxo-1,3,4-thiadiazol-2-yl)-2,3,4,5,6-pentafluoro-[(1-oxo-3-phenylpropyl)amino]benzenepropanamide

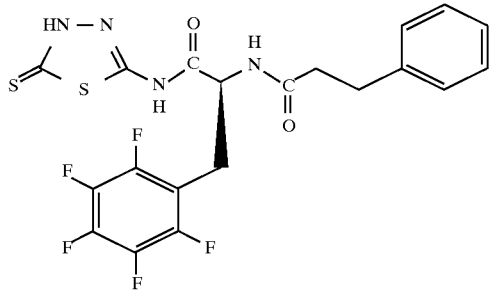

Following the general procedure outlined in method B, and making non critical variations but starting with Boc-pentafluoro-L-phenylalanine, the title compound is obtained.

$^1$H NMR (DMSO) δ:2.39–2.42, 2.68–2.73, 3.03, 3.14, 4.81, 7.12–7.22, 8.43–8.45, 12.7, 14.1.

MS(FAB): m/z: 503, 370, 210, 134, 133, 105, 91.

EXAMPLE 31

Preparation of (S)-[1-[[(4,5-dihydro-5-thioxo-1,3,4-thiadiazol-2-yl)amino]carbonyl]-1,4-butanediyl]bis carbamic acid bis(phenylmethyl) ester

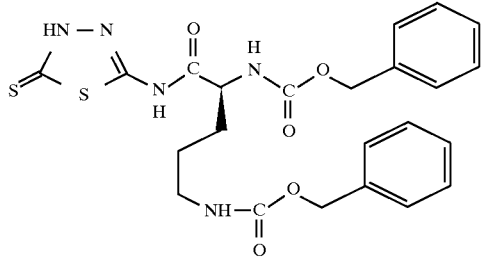

Following the general procedure outlined in method B, and making non critical variations but starting with di-N-benzyloxycarbonyl-L-ornithine, the title compound is obtained.

$^1$H NMR (DMSO) δ: 1.4–1.7, 2.98, 4.15, 4.98–5.00, 7.21, 7.31–7.33, 7.76, 12.6, $^{13}$C NMR (DMSO) ppm: 184, 172.7, 156.5, 152.41, 137.67, 137.24, 128.8, 128.25, 128.19, 66.13, 65.64, 54.71, 28.99, 26.44.

MS(FAB): m/z: 516, 408, 91.

EXAMPLE 32

Preparation of (S)-N-[1-[[(4,5-dihydro-5-thioxo-1,3,4-thiadiazol-2-yl)amino]carbonyl]-2,2-dimethylpropyl]-(1H-indole-3-acetamide

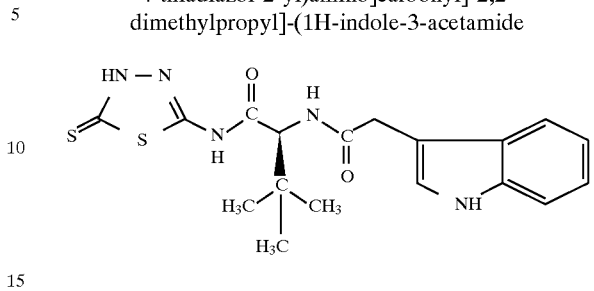

Following the general procedure outlined in method B, and making non critical variations but starting with 3-indoleacetic acid, the title compound is obtained.

$^1$H NMR (DMSO) δ:0.895, 3.6–3.65, 4.39–4.44, 6.92, 7.03, 7.15, 7.29, 7.51, 8.11, 10.8, 12.6, 14.1.

MS (EI): m/z: 403, 271, 243, 157, 130, 86.

EXAMPLE 33

Preparation of (S)-[2-[(4,5-dihydro-5-thioxo-1,3,4-thiadiazol-2-yl)amino]-1-(1H-indol-3-yl-methyl)-2-oxoethyl]-carbamic acid, phenylmethyl ester

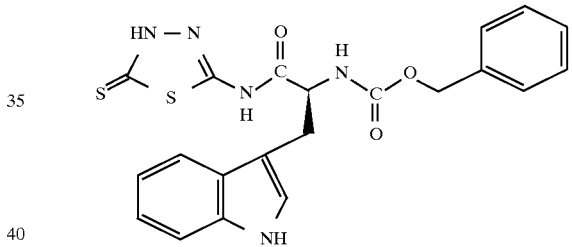

5-Amino-1,3,4-thiadiazole-2-thione (765 mg, 5.74 mmol) and diisopropylethylamine (1.0 ml, 5.74 mmol) are added to a solution of CBZ-(L)-tryptophan N-hydroxysuccinimide ester (2.5 g, 5.74 mmol) in anhydrous THF (25 mL) in an oven dried flask under nitrogen. The reaction is stirred at ambient temperature for four days, then the solvent is removed in vacuo. The reaction is quenched with aqueous citric acid (1M), extracted into CH$_2$Cl$_2$, dried over MgSO$_4$, and concentrated to give a 2.54 g yellow foam. Chromatography (MeOH/CH$_2$Cl$_2$), followed by recrystallization (CH$_2$Cl$_2$) provides the title compound as a white solid.

$^1$H NMR (DMSO-d$_6$) δ 3.01, 3.17, 4.52, 4.97, 6.98, 7.08, 7.20–7.36, 7.70, 7.81, 10.88, 12.77, 14.11;

$^{13}$C NMR (DMSO-d$_6$) ppm 27.2, 55.3, 65.5, 108.9, 111.3, 118.2, 118.5, 120.9, 124.2, 126.9, 127.6, 127.7, 128.0, 128.2, 135.9, 136.6, 151.9, 155.3, 172.2, 183.6;

IR (mull) 3411, 3389, 3322, 1951, 1687, 1567, 1536, 1309, 1275, 1265, 1250, 1066, 1058, 744, 738 cm$^{-1}$;

MS (FAB) m/z 454 (M+), 562, 532, 531, 530, 456, 455, 454, 453, 130, 91;

[α]$_D$ (DMSO)=+85°.

EXAMPLE 34

Preparation of (S)-[2-[(4,5-dihydro-5-thioxo-1,3,4-thiadiazol-2-yl)amino]-2-oxo-1-(phenylmethyl)ethyl]carbamic acid phenylmethyl ester

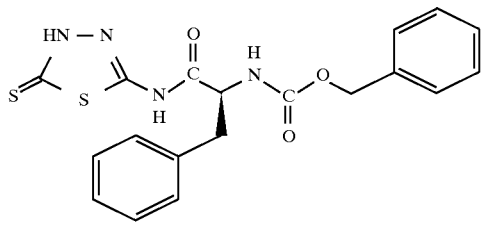

To a well stirred solution of (L)-Cbz-phenylalanine p-nitrophenyl ester (840 mg, 2.0 mmol) and 5-amino-1,3,4-thiadiazole-2-thione (266 mg, 2.0 mmol) in anhydrous DMF, at room temperature, is added triethylamine (202 mg, 2.0 mmol) via syringe. The reaction mixture is stirred at room temperature for 48 hours, poured into water and extracted repeatedly with dichloromethane. The resulting extracts are combined, dried (anhydrous sodium sulfate) and concentrated to give a residue which is chromatographed on silica gel (elution with 10% methanol/dichloromethane). A material is obtained which contains both the desired material and an impurity. This is rechromatograped on silica (elution with 5% methanol/dichloromethane) to provide the title compound as a white solid.

$^1$H NMR (DMSO-d$_6$) 2.73–2.87, 3.00–3.10, 4.49, 4.97, 7.22–7.34, 7.92, 12.75, 14.13;

$^{13}$C NMR (DMSO-d$_6$) ppm 36.83, 56.27, 65.65, 126.68, 127.72, 127.89, 128.26, 128.39, 129.31, 152.04, 156.08, 171.93, 183.79;

IR (mull) 3214, 3131, 2350, 2190, 2123, 1996, 1941, 1677, 1579, 1497, 1336, 1304, 1289, 1065, 1053 cm$^{-1}$;

MS (EI) m/z 414 (M+), 414, 223, 120, 108, 92, 91, 79, 77, 65, 51;

$[\alpha]_D$ (DMSO)=+64 °

EXAMPLE 35

Preparation of (S)-[1-[[(4,5-dihydro-5-thioxo-1,3,4-thiadiazol-2-yl)amino]carbonyl]-3-methylbutyl]carbamic acid phenylmethyl ester

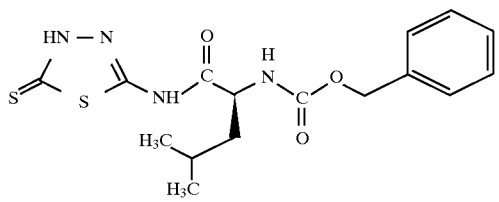

5-Amino-1,3,4-thiadiazole-2-thione (809 mg, 6.1 mmol) and diisopropylethylamine (1.4 mL, 8.3 mmol) are added to a solution of CBZ-(L)-leucine N-hydroxysuccinimide ester (2.0 g, 5.5 mmol), in anhydrous THF (25 mL) and in a flame dried flask under nitrogen. The reaction is heated to reflux and stirred overnight. The solvent is removed in vacuo, and the resulting oil is dissolved in ethyl acetate (100 mL). The organic solution is washed with aqueous citric acid (1M, 3×75 mL), dried over MgSO$_4$, and adhered to silica gel. Chromatography (MeOH/CH$_2$Cl$_2$) provides the product as a cream foam, 1.68 g (64%).

$^1$H NMR (DMSO-d$_6$) δ 0.85, 1.53, 4.24, 5.00, 7.33, 7.73, 12.68, 14.12;

$^{13}$C NMR (DMSO-d$_6$) ppm 21.1, 23.0, 24.3, 53.0, 59.8, 65.7, 127.8, 127.9, 128.4, 136.8, 152.1, 156.1, 172.9, 183.7;

IR (mull) 3183, 3119, 3031, 1954, 1689, 1575, 1526, 1498, 1341, 1302, 1267, 1227, 1068, 1046, 697 cm$^{-1}$;

MS (EI) m/z 380 (M+), 380, 223, 176, 133, 92, 91, 86, 79, 65;

$[\alpha]_D$ (DMSO)=+23°.

EXAMPLE 36

Preparation of (S)-[1-[[(4,5-dihydro-5-thioxo-1,3,4-thiadiazol-2-yl)amino]carbonyl]-2-methylpropyl] carbamic acid phenylmethyl ester

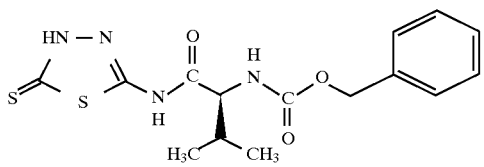

5-Amino-1,3,4-thiadiazole-2-thione (765 mg, 5.74 mmol) and diisopropylethylamine (1.0 ml, 5.74 mmol) are added to a solution of CBZ-(L)-valine N-hydroxysuccinimide ester (2.0 g, 5.74 mmol) in anhydrous THF (25 mL), in an oven dried flask under nitrogen. The reaction is stirred at ambient temperature overnight, whereupon the solvent is removed in vacuo. The residual oil is dissolved in ethyl acetate, washed with aqueous citric acid (1M), dried over MgSO$_4$, and concentrated to give a 3.22 g foamy oil. Chromatography (MeOH/CH$_2$Cl$_2$, 31% chromatographed yield), followed by recrystallization (CH$_2$Cl$_2$) provides the title compound as a white solid. mp 179°–180° C.

$^1$H NMR (DMSO-d$_6$) δ0.89, 2.02, 4.09, 5.04, 7.24–7.38, 7.74, 12.62, 14.11;

$^{13}$C NMR (DMSO-d$_6$) ppm 18.2, 18.9, 29.8, 60.0, 65.6, 127.7, 128.0, 128.3, 136.7, 151.7, 156.2, 171.7, 183.6;

IR (mull) 3271, 3209, 2339, 2134, 1996, 1946, 1706, 1684, 1666, 1583, 1411, 1335, 1297, 1072, 1068 cm$^{-1}$;

MS (EI) m/z 366 (M+), 366, 223, 162, 108, 92, 91, 79, 72, 65, 55;

$[\alpha]_D$ (DMSO)=−28°.

EXAMPLE 37

Preparation of (S)-[1-[[(4,5-dihydro-5-thioxo-1,3,4-thiadiazol-2-yl)amino]carbonyl]-2,2-dimethylpropyl] carbamic acid 9H-fluoren-9-yl-methyl ester

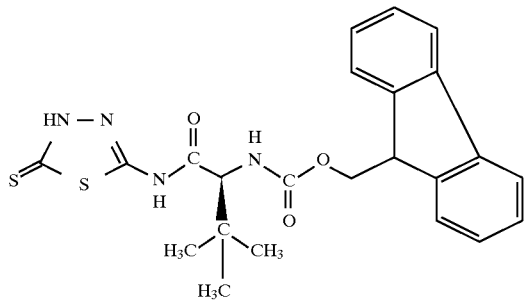

Following the general procedure outlined in method B, and making non critical variations but starting with FMOC L-tert-butylglycine, the title compound is obtained as a white solid.

¹H NMR (DMSO-d₆) δ 0.95, 4.17–4.28, 7.29, 7.39, 7.73, 7.86, 12.58, 14.10;

¹³C NMR (DMSO-d₆) ppm 26.9, 34.5, 47.1, 62.9, 66.5, 120.6, 125.9, 127.5, 128.1, 141.2, 144.2, 152.0, 156.8, 171.3, 184.2;

IR (mull) 3197, 3119, 3067, 2324, 1996, 1949, 1911, 1671, 1576, 1528, 1297, 1257, 1068, 758, 741 cm⁻¹.

MS (EI) m/z 468 (M+), 468, 290, 180, 179, 178, 166, 165, 133, 130, 86;

$[\alpha]_D$ (DMSO)=−103°.

Preparation of N-Protected β-Amino Acids

EXAMPLE 38

Preparation of [3-[(4,5-dihydro-5-thioxo-1,3,4-thiadiazol-2-yl)amino]-3-oxo-2-phenylpropyl]carbamic acid phenylmethyl ester

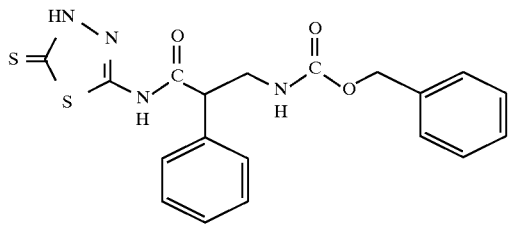

Following the general procedure outlined in method A, and making non critical variations but starting with 2-phenyl-3-[[(phenylmethoxy)carbonyl]amino]propionic acid, the title compound is obtained as a white solid. mp 201°–2° C.

¹H NMR (DMSO) δ 3.61, 4.11, 4.97, 5.04, 7.29–7.35, 7.56, 12.68, 14.07;

13C NMR (DMSO) ppm 43.20, 50.86, 65.40, 127.75, 127.88, 127.93, 128.14, 128.52, 128.92, 136.68, 137.29, 152.10, 156.40, 171.53, 183.84;

IR (mull) 3138, 2344, 2127, 1964, 1688, 1654, 1579, 1555, 1434, 1302, 1285, 1175, 1070, 1061, 765 cm⁻¹;

MS (EI) m/z 414 (M+), 250, 223, 118, 103, 92, 91, 90, 79, 77, 65.

EXAMPLE 39

Preparation of [3-[(4,5-dihydro-5-thioxo-1,3,4-thiadiazol-2-yl)amino]-3-oxo-2-(phenylmethyl)propyl]carbamic acid phenylmethyl ester

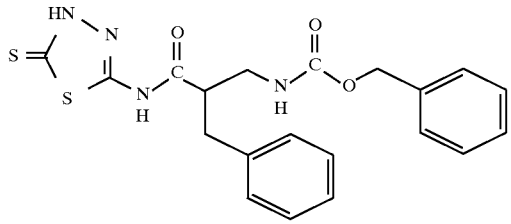

Following the general procedure outlined in method A, and making non critical variations but starting with 2-(phenylmethyl)-3-[[(phenylmethoxy)carbonyl]amino]propionic acid, the title compound is obtained as a white solid. mp 88°–90° C. decompose.

¹H NMR (DMSO) δ 2.70, 2.83, 2.98, 3.20, 4.91, 4.97, 7.12–7.16, 7.20–7.30, 7.46, 12.38, 14.00;

¹³C NMR (DMSO) ppm 35.17, 41.92, 47.64, 65.24, 126.33, 127.65, 127.74, 128.30, 128.76, 137.05, 138.43, 152.00, 156.16, 172.80, 183.54;

IR (mull) 3255, 3170, 2344, 2187, 1946, 1683, 1669, 1573, 1546, 1496, 1301, 1285, 1260, 1063, 697 cm⁻¹;

MS (EI) m/z 428 (M+), 428, 296, 277, 223, 145, 133, 117, 115, 92, 91.

EXAMPLE 40

Preparation of [3-[(4,5-dihydro-5-thioxo-1,3,4-thiadiazol-2-yl)amino]-3-oxo-1-(1,1-dimethylethyl)propyl]carbamic acid phenylmethyl ester

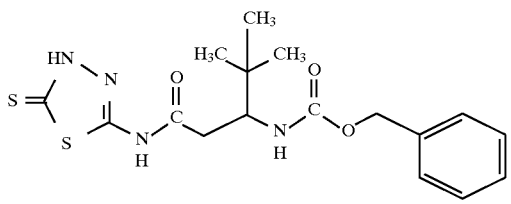

Following the general procedure outlined in method A, and making non critical variations but starting with 3-[[(phenylmethoxy)carbonyl]amino]-4,4-dimethylpentanoic acid, the title compound is obtained as a yellow solid.

¹H NMR (DMSO) δ 0.85, 2.38, 2.70, 3.85, 4.90, 5.09, 7.17, 7.25–7.35, 12.36, 14/07;

IR (mull) 3300, 3090, 2190, 2024, 1951, 1697, 1672, 1577, 1320, 1297, 1287, 1272, 1255, 1060, 1020 cm⁻¹;

MS (EI) m/z 394 (M+), 395, 394, 262, 223, 133, 92, 91, 70, 65, 57.

EXAMPLE 41

Preparation of [3-[(4,5-dihydro-5-thioxo-1,3,4-thiadiazol-2-yl)amino]-3-oxo-1-phenylpropyl]carbamic acid phenylmethyl ester

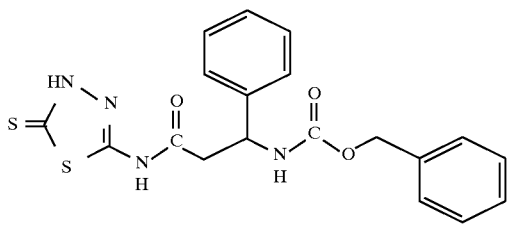

Following the general procedure outlined in method A, and making non critical variations but starting with 3-phenyl-3-[[(phenylmethoxy)carbonyl]amino]propionic acid, the title compound is obtained as a white solid. mp 222°–3° C.

¹H NMR (DMSO) δ2.80, 4.88, 4.97, 5.03, 7.18–7.28, 7.95, 12.40, 14.02;

¹³C NMR (DMSO) ppm 42.01, 51.16, 65.21, 126.16, 127.08, 127.55, 127.68, 128.21, 128.30, 136.93, 142.32, 151.89, 155.28, 169.30, 183.45;

IR (mull) 3269, 3028, 1961, 1691, 1670, 1581, 1562, 1442, 1313, 1305, 1263, 1070, 753, 696, 603 cm⁻¹;

MS (EI) m/z 414 (M+), 414, 223, 131, 106, 104, 92, 91, 79, 77, 65.

EXAMPLE 42

Preparation of β-(benzoylamino)-N-(4,5-dihydro-5-thioxo-1,3,4-thiadiazol-2-yl)benzenepropanamide

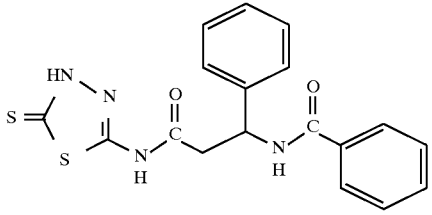

Following the general procedure outlined in method A, and making non critical variations but starting with β-(benzoylamino)-β-phenylpropanoic acid, the title compound is obtained as a white solid. mp. 266°–7° C. decompose.

$^1$H NMR (DMSO) δ 3.05, 5.55, 7.25–7.27, 7.32–7.37, 7.42–7.54, 7.83–7.85, 8.98, 12.53, 14.09;

$^{13}$C NMR (DMSO) ppm 43.32, 51.43, 128.22, 128.84, 129.08, 130.00, 130.11, 133.03, 136.12, 144.19, 153.76, 167.49, 171.33, 185.26;

IR (mull) 3358, 3352, 3192, 2346, 1960, 1675, 1637, 1568, 1528, 1419, 1402, 1296, 1056, 703, 601 cm$^{-1}$;

MS (EI) m/z 384 (M+), 384, 253, 252, 210, 131, 106, 105, 104, 103, 77.

EXAMPLE 43

Preparation of N-(4,5-dihydro-5-thioxo-1,3,4-thiadiazol-2-yl)-β-[(phenylacetyl)amino]benzenepropanamide

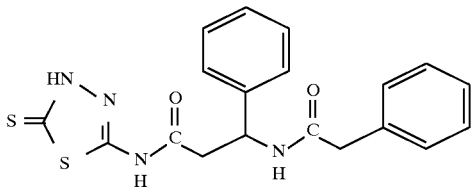

Following the general procedure outlined in method A, and making non critical variations but starting with β-[(phenylacetyl)amino]-β-phenylpropanoic acid, the title compound is obtained as a white solid. mp 249°–50° C. decompose.

$^1$H NMR (DMSO) δ 2.84, 2.95, 3.40, 3.47, 5.34, 7.17–7.26, 7.32–7.34, 8.72, 12.47, 14.09;

$^{13}$C NMR (DMSO) ppm 43.70, 44.01, 51.00, 128.01, 128.07, 128.86, 129.82, 130.12, 130.60, 138.03, 143.78, 153.72, 171.11, 185.32;

IR (mull) 3266, 3104, 3065, 2344, 2186, 1955, 1663, 1643, 1584, 1552, 1493, 1291, 1060, 745, 695 cm$^{-1}$;

MS (EI) m/z 398 (M+), 398, 267, 266, 224, 132, 131, 106, 104, 103, 91.

EXAMPLE 44

Preparation of N-(4,5-dihydro-5-thioxo-1,3,4-thiadiazol-2-yl)-β-[(phenyloxyacetyl)amino]benzenepropanamide

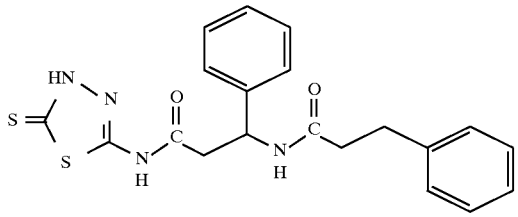

Following the general procedure outlined in method A, and making non critical variations but starting with β-[(phenyloxyacetyl)amino]benzenepropanoic acid, the title compound is obtained as a pale yellow solid. mp 269° C. decompose.

$^1$H NMR (DMSO) δ 6 2.37, 2.76, 2.78, 2.88, 5.30, 7.12–7.31, 8.38, 12.40, 13.99;

$^{13}$C NMR (DMSO) ppm 31.49, 37.36, 42.32, 49.52, 126.29, 126.84, 127.50, 128.64, 128.68, 128.79, 141.65, 142.54, 152.47, 169.86, 171.17, 184.05;

IR (mull) 3243, 3114, 2810, 2790, 1666, 1616, 1579, 1549, 1509, 1434, 1300, 1290, 783, 745, 699 cm$^{-1}$;

MS (EI) m/z (rel. intensity) 412, 280, 238, 132, 131, 106, 105, 104, 103, 91, 77.

EXAMPLE 45

Preparation of [3-[(4,5-dihydro-5-thioxo-1,3,4-thiadiazol-2-yl)amino]-3-oxo-1-phenylpropyl]carbamic acid 1,1-dimethylethyl ester

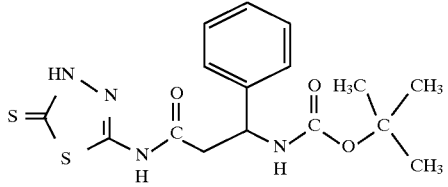

Following the general procedure outlined in method A, and making non critical variations but starting with β-[[(1,1-dimethylethoxy)carbonyl]amino]-benzenepropanoic acid, the title compound is obtained as a white solid. mp 248°–9° C. decompose.

$^1$H NMR (DMSO) δ 1.33, 2.78–2.82, 4.97–5.08, 7.20–7.25, 7.31–7.32, 7.53, 12.42, 14.07;

$^{13}$C NMR (DMSO) ppm 29.90, 44.02, 52.66, 79.79, 127.98, 128.74, 130.03, 144.58, 15.02, 156.61, 171.23, 185.35;

IR (mull) 3104, 2405, 2289, 2124, 1949, 1696, 1669, 1573, 1537, 1305, 1290, 1280, 1161, 1071, 699 cm$^{-1}$;

MS (EI) m/z 380 (M+), 380, 324, 280, 159, 150, 133, 131, 106, 104, 57.

EXAMPLE 46

Preparation of [3-[(4,5-dihydro-5-thioxo-1,3,4-thiadiazol-2-yl)amino]-3-oxo-1-phenylpropyl] carbamic acid 9H-fluoren-9-yl methyl ester

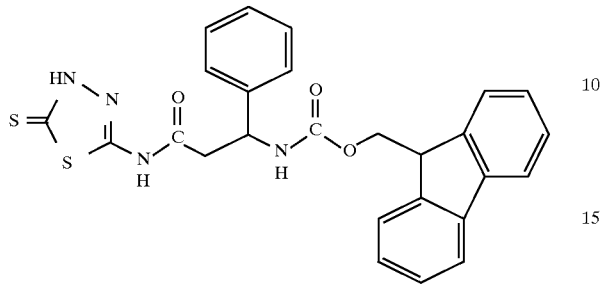

Following the general procedure outlined in method A, and making non critical variations but starting with N-Fmoc-3-amino-3-phenylpropanoic acid, the title compound is obtained as a white solid.

$^1$H NMR (DMSO) δ 2.88, 4.18–4.27, 4.31–4.37, 5.04–5.11, 7.24–7.44, 7.64–7.68, 7.86–7.88, 8.03, 12.49, 14.09;

IR (mull) 3089, 3020, 1951, 1909, 1694, 1666, 1576, 1551, 1496, 1298, 1267, 1072, 1058, 745, 698 cm$^{-1}$;

MS (EI) m/z 196, 179, 178, 176, 166, 165, 163, 106, 104, 76.

EXAMPLE 47

Preparation of N-(4,5-dihydro-5-thioxo-1,3,4-thiadiazol-2-yl)-β-[(methoxyacetyl)amino] benzenepropanamide

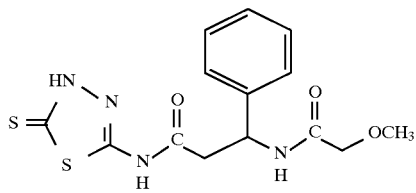

Following the general procedure outlined in method A, and making non critical variations but starting with β-[(methoxyacetyl)amino]benzenepropanoic acid, the title compound is obtained as a white solid. mp 241°–2° C.

$^1$H NMR (DMSO) δ 2.89–3.03, 3.26, 3.78, 5.34–5.36, 7.21–7.32, 8.37, 12.43, 14.04;

$^{13}$C NMR (DMSO) ppm 41.74, 49.18, 58.98, 71.94, 126.94, 127.59, 128.81, 142.53, 152.41, 168.88, 170.10, 184.04;

IR (mull) 3318, 3097, 1679, 1672, 1651, 1575, 1546, 1496, 1415, 1301, 1194, 1116, 1071, 750, 699 cm$^{-1}$;

MS (EI) m/z 352 (M+) 352, 220, 178, 132, 131, 118, 104, 103, 77, 45.

EXAMPLE 48

Preparation of N-(4,5-dihydro-5-thioxo-1,3,4-thiadiazol-2-yl)-β-[(phenoxyacetyl)amino] benzenepropanamide

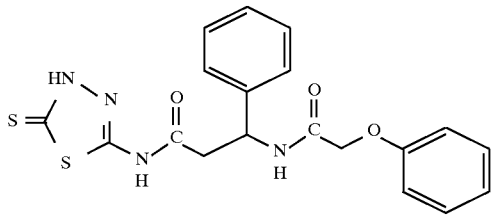

Following the general procedure outlined in method A, and making non critical variations but starting with β-[(phenoxyacetyl)amino]benzenepropanoic acid, the title compound is obtained as a white solid. mp 225°–6° C.

$^1$H NMR (DMSO) δ 2.95, 4.47, 5.38, 6.88–6.95, 7.21–7.31, 8.64, 12.42, 14.03;

$^{13}$C NMR (DMSO) ppm 41.80, 49.34, 67.45, 115.23, 121.62, 126.90, 127.64, 128.82, 129.86, 140.30, 142.27, 152.40, 167.65, 169.96, 184.06;

IR (mull) 3343, 1685, 1647, 1599, 1586, 1571, 1529, 1494, 1484, 1309, 1207, 1081, 1066, 757, 704 cm$^{-1}$;

MS (EI) m/z 414 (M+) 414, 282, 240, 131, 118, 107, 104, 103, 79, 77.

EXAMPLE 49

Preparation of N-(4,5-dihydro-5-thioxo-1,3,4-thiadiazol-2-yl)-β-[(phenylmethoxyacetyl)amino] benzenepropanamide

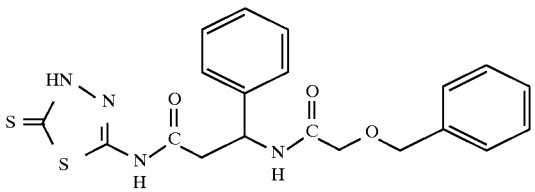

Following the general procedure outlined in method A, and making non critical variations but starting with β-[(phenylmethoxyacetyl)amino]-benzenepropanoic acid, the title compound is obtained as a white solid. mp 190°–1° C.

$^1$H NMR (DMSO) δ 2.92, 3.00, 3.88, 4.49, 5.33–5.40, 7.20–7.33, 8.43, 12.46, 14.06;

$^{13}$C NMR (DMSO) ppm 41.71, 49.27, 69.59, 72.66, 126.90, 127.61, 128.14, 128.23, 128.75, 128.83, 138.08, 142.41, 152.40, 168.86, 170.18, 184.07;

IR (mull) 3350, 3333, 3197, 2343, 1996, 1970, 1698, 1673, 1652, 1574, 1569, 1528, 1312, 1295, 1071 cm$^{-1}$;

MS (EI) m/z 428 (M+), 296, 254, 131, 106, 104, 103, 92, 91, 77, 65.

EXAMPLE 50

Preparation of methyl (S)-β-[[(phenylmethoxy)carbonyl]amino]benzenepropanoate and methyl (R)-β-[[(phenylmethoxy)carbonyl]amino]benzenepropanoate

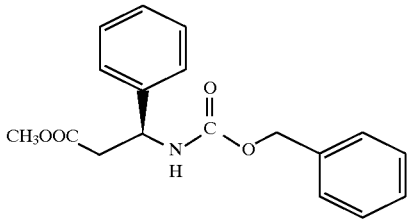

Methyl-β-[[(phenylmethoxy)carbonyl]amino]-benzenepropanoate (4.87 g), prepared from 3-amino-3-phenylpropionic acid via standard methods, is separated by chiral HPLC [(R,R)-Whelk-O 1 column, elution with 40% isopropyl alcohol in hexane) to give 2.20 g of methyl (S)-β-[[(phenylmethoxy)carbonyl]amino]benzenepropanoate and 2.33 g methyl (R)-β-[[(phenylmethoxy)carbonyl]amino]benzenepropanoate. Each enantiomer is analyzed at >99% ee. Data for (S)-configuration enantiomer $^1$H NMR (CDCl$_3$) δ 2.81–2.96, 3.60, 5.07, 5.12, 5.16–5.21, 5.76, 7.23–7.36;

$^{13}$C NMR (CDCl$_3$) ppm 40.51, 51.70, 51.84, 66.92, 126.16, 127.71, 128.15, 128.53, 128.75, 136.39, 140.79, 155.60, 171.27;

IR (mull) 3381, 3367, 1740, 1720, 1535, 1512, 1444, 1295, 1246, 1227, 1173, 1025, 992, 757, 700 cm$^{-1}$;

MS (EI) m/z 313 (M+) 178, 164, 121, 108, 107, 104, 92, 91, 77, 65.

$[α]_D$ (CHCl$_3$)=−19°.

Data for (R)-configuration enantiomer

1H NMR (CDCl$_3$) δ 2.80–2.85, 3.60, 5.08, 5.12, 5.16–5.20, 5.76, 7.24–7.36;

$^{13}$C NMR (CDCl$_3$) ppm 40.51, 51.70, 51.84, 66.91, 126.16, 127.71, 128.14, 128.52, 128.75, 136.39, 140.77, 155.60, 171.26;

IR (mull) 3381, 3367, 1740, 1720, 1535, 1512, 1444, 1295, 1246, 1227, 1173, 1025, 992, 757, 700 cm$^{-1}$;

MS (EI) m/z 313 (M+) 178, 164, 121, 108, 107, 104, 92, 91, 77, 65. $[α]_D$ (CHCl$_3$)=+20°.

EXAMPLE 51

Preparation of (S)-[3-[(4,5-dihydro-5-thioxo-1,3,4-thiadiazol-2-yl)amino]-3-oxo-1-phenylpropyl]carbamic acid phenylmethyl ester

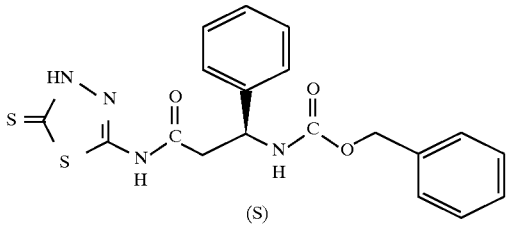
(S)

Step 1

Preparation of (S)-β-[[(phenylmethoxy)carbonyl]amino]benzenepropanoic acid

A solution of (S)-β-[[(phenylmethoxy)carbonyl]amino]-benzenepropanoate (1.60 g, 5.11 mmol), 1 M NaOH (25 mL) and THF (25 mL) is stirred 18 hours at ambient temperature. The reaction is concentrated in vacuo to remove THF, the residue diluted with 30 mL H$_2$O, and washed with (3×25 mL) Et$_2$O. The aqueous phase is brought to pH=3 with concentration. HCl and the resulting precipitate collected and dried to afford 1.40 g (4.69 mmol, 92%) product as a white solid. mp 135° C.

$^1$H NMR (DMSO) δ 2.60, 2.69, 4.90–5.02, 7.20–7.31, 7.89, 12.23;

$^{13}$C NMR (DMSO) ppm 41.64, 52.14, 65.79, 126.84, 127.50, 128.20, 128.26, 128.78, 128.80, 137.52, 143.32, 155.80, 172.15;

IR (mull) 3362, 3036, 1696, 1529, 1287, 1251, 1234, 1050, 1033, 1028, 753, 733, 706, 699, 618 cm$^{-1}$;

MS (EI) m/z 299 (M+) 196, 164, 150, 108, 107, 104, 91, 79, 77, 65.

Step 2

Preparation of (S)-[3-[(4,5-dihydro-5-thioxo-1,3,4-thiadiazol-2-yl)amino]-3-oxo-1-phenylpropyl]carbamic acid phenylmethyl ester Following the general procedure outlined in method A, and making non critical variations but starting with (S)-β-[[phenylmethoxy)carbonyl]amino]benzenepropanoic acid, the title compound is obtained as a white solid.

IR (mull) 3356, 3346, 3215, 1693, 1676, 1586, 1569, 1525, 1421, 1254, 1057, 1046, 600;

$^1$H NMR (DMSO) δ 2.83–2.86, 4.92, 5.02, 5.04–5.11, 7.22–7.32, 7.96, 12.43, 14.02;

MS (EI) m/z 414 (M+) 414, 282, 239, 223, 133, 131, 106, 104, 92, 91.

$[α]_D$ (THF)=+15°.

EXAMPLE 52

Preparation of (R)-[3-[(4,5-dihydro-5-thioxo-1,3,4-thiadiazol-2-yl)amino]-3-oxo-1-phenylpropyl]carbamic acid phenylmethyl ester

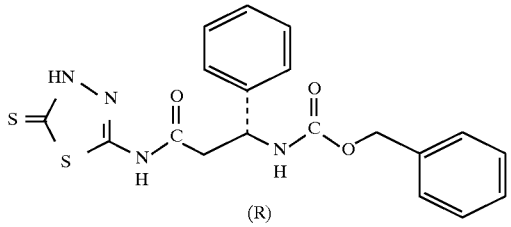
(R)

Step 1

Preparation of (R)-β-[[(phenylmethoxy)carbonyl]amino]-benzenepropanoic acid

Following the procedure in Example 55, Step 1, and making non critical variations but starting with (R)-β-[[(phenylmethoxy)carbonyl]amino]benzenepropanoate, the title compound is obtained as a white solid.

$^1$H NMR (CDCl$_3$) δ 2.83–3.02, 5.07, 5.12, 5.13–5.21, 7.26–7.32;

IR (mull) 3362, 3036, 1697, 1529, 1287, 1251, 1244, 1234, 1049, 1033, 1027, 753, 706, 699, 618 cm$^{-1}$;

MS (EI) m/z 299 (M+) 164, 150, 108, 107, 104, 92, 91, 79, 77, 65.

Step 2

Preparation of (R)-[3-[(4,5-dihydro-5-thioxo-1,3,4-thiadiazol-2-yl)amino]-3-oxo-1-phenylpropyl]carbamic acid phenylmethyl ester Carbonyldiimidazole (0.879 g, 5.42 mmol) is added to a solution of (R)-β-[[(phenylmethoxy)carbonyl]amino]

benzenepropanoic acid (1.08 g, 3.62 mmol) in 25 mL THF under N₂ at room temperature and allowed to stir for 0.5 hours. Diisopropylethylamine (0.63 mL, 3.6 mmol) and 5-amino-1,3,4-thiadiazole-2-thiol (0.482 g, 3.62 mmol) are added and the reaction is stirred at ambient temperature for 18 hours. The reaction is concentrated in vacuo, diluted with 50 mL CH₂Cl₂, and washed with (3×25 mL) 1 M citric acid. The organic phase is dried (Na₂SO₄), combined with the precipitate that formed in the aqueous phase, absorbed onto silica gel and chromatographed (2–5% MeOH/CH₂Cl₂). The precipitate which formed in the fractions containing product is collected and dried to afford 0.217 g product as white needles.

IR (mull) 3356, 3346, 3215, 1693, 1676, 1586, 1569, 1525, 1421, 1321, 1300, 1254, 1057, 1046, 600;

¹H NMR (DMSO) δ 2.83–2.86, 4.93, 5.01, 5.04–5.11, 7.22–7.32 , 7.96, 12.41, 14.04;

MS (EI) m/z 414 (M+) 159, 133, 131, 106, 104, 103, 92, 91, 79, 77.

[α]$_D$ (THF)=–18°.

EXAMPLE 53

(1S-cis-)-[2-[[(4,5-dihydro-5-thioxo-1,3,4-thiadiazol-2-yl)amino]carbonyl]cyclohexyl]carbamic acid 9H-fluoren-9-yl-methyl ester

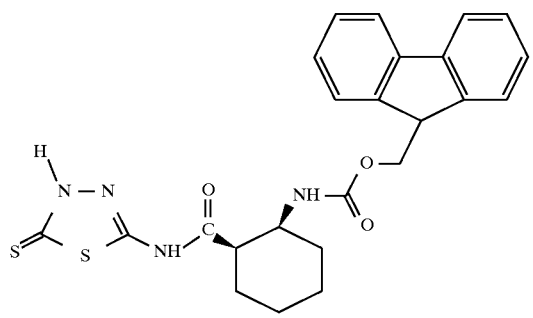

Step 1

Preparation of cis-(N-9-fluorenylmethoxycarbonyl)-2-amino cyclohexane carboxylic acid The title compound is prepared according to the procedure described in *J. Med Chem.*, Vol. 36, pp 1100–1103 (1993), and starting with cis-2-aminocyclohexane carboxylic acid which can be prepared according to the procedure described in *Chem Ber.*, Vol. 92, pp 1594–1599 (1959).

¹H NMR (CD₃OD) δ 1.35–175, 1.80–1.85, 1.9–2.05, 2.7, 3.95–4.05, 4.2–4.4, 7.32–7.43, 7.64–7.66, 7.80–7.82.

Step 2

Preparation of (1S-cis-)-[2-[[(4,5-dihydro-5-thioxo-1,3,4-thiadiazol-2-yl)-amino]carbonyl]cyclohexyl] carbamic acid 9H-fluoren-9-yl-methyl ester Following the general procedure outlined in method B, and making non critical variations but starting with cis-(N-9-fluorenylmethoxycarbonyl)-2-aminocyclohexane carboxylic acid, the title compound is obtained.

¹H NMR (DMSO) δ: 1.2–1.9, 2.77, 4.06–4.20, 4.30–4.34, 7.27–7.47, 7.63–7.72, 7.86–7.89, 12.3–12.4, 13.9–14.1.

MS(EI): m/z: 480, 302, 284, 258, 178, 152, 133.

EXAMPLE 54

(S)-[1-[2-[[4,5-dihydro-5-thioxo-1,3,4-thiadiazol-2-yl)amino]-2-oxoethyl]-3-methylbutyl]carbamic acid phenylmethyl ester

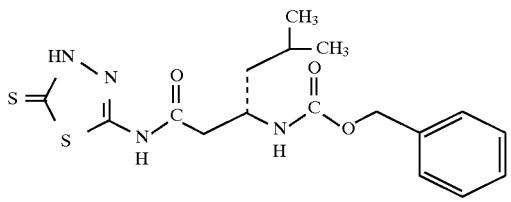

Step 1

Preparation of (S)-3-benzyloxycarbonylamino-3-isobutylbutyric acid

The title compound is synthesized according to the procedure described in *Liebigs Ann.*, pp 1217–1228 (1995).

Step 2

Preparation of (S)-[1-[2-[(4,5-dihydro-5-thioxo-1,3,4-thiadiazol-2-yl)-amino]-2-oxoethyl]-3-methylbutyl]carbamic acid phenylmethyl ester Following the general procedure outlined in method B, and making non-critical variations, but starting with (S)-3-benzyloxycarbonylamino-3-isobutyl-butyric acid, the title compound is prepared.

¹H NMR (DMSO) δ: 0.82–0.84, 1.13–1.17, 1.36–1.39, 1.45–1.58, 2.42–2.56, 3.97–4.02, 4.90–5.03, 7.18–7.31, 12.4, 14.1.

MS (EI): m/z: 394, 262, 243, 111, 91.

EXAMPLE 55

(R*,S*)-[2-[[(4,5-dihydro-5-thioxo-1,3,4-thiadiazol-2-yl)amino]carbonyl]-1-(2-methylpropyl)-4-pentenyl]carbamic acid phenylmethyl ester

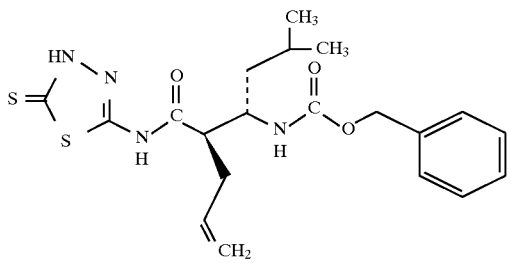

Step 1

Preparation of methyl (2S,3S)-2-allyl-3-benzyloxycarbonylamino-3-isobutyl-butanoate 500 mg (1.71 mmol) of methyl(S)-3-benzyloxycarbonylamino-3-isobutyl-butanoate, prepared according to the procedure described in *Liebigs Ann.*, pp 1217–1228 (1995), is dissolved in 10 mL of dry THF and cooled under Argon to –80° C. 1.881 mL (3.762 mmol) of 2M LDA is added, and the mixture is stirred at –40° C. for 20 minutes. The reaction is cooled to –78° C., and 828 mg (6.84 mmol) of allyl bromide are added. The mixture is stirred at –78° C. for 5 hours and at room temperature overnight. The reaction is quenched with 20 mL of 1M pH 7 phosphate buffer. The pH is lowered to 2 with 1N HCl. The water layer is extracted with EtOAc. The combined organic layers are dried over MgSO$_4$, and concentrated to provide the crude product, which is purified by chromatography using 70% hexanes/30% EtOAc as eluant to give the title compound.

Step 2

Preparation of (2S,3S)-2-allyl-3-benzyloxycarbonylamino-3-isobutylbutyric acid 221 mg of the methyl ester from Step 1 are hydrolyzed by treatment with 5 mL of 1N KOH and 5 mL of MeOH for 4 hours at room temperature. The solution is made acidic with 1N HCl. Most of the MeOH is removed and the product is extracted into EtOAC. The product is purified by flash chromatography on silica gel using 70% hexanes/28% EtOAc/2% HOAc to give the title compound.

Step 3

Preparation of methyl (2S,3S)-2-allyl-3-benzyloxycarbonylamino-3-isobutyl-butanoate Following the general procedure outlined in method B, and making non-critical variations but starting with the product of Step 2, the title compound is obtained.

$^1$H NMR (DMSO) δ: 0.799–0.812, 1.17–1.3, 1.45–1.6, 2.29, 2.67, 3.7–3.82, 4.95–5.01, 5.55–5.75, 6.98–7.01, 7.25–7.28, 12.4, 14.1.

MS (EI): m/z: 434, 326, 302, 300, 220, 159, 133, 91, 86.

EXAMPLE 56

(R*,S*)-[1-[2-[(4,5-dihydro-5-thioxo-1,3,4-thiadiazol-2-yl)amino]-oxo-1(phenylmethyl)ethyl]-3-methylbutyl]carbamic acid phenylmethyl ester

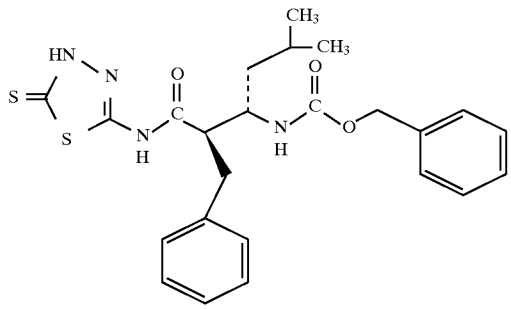

Step 1

Preparation of methyl (2S,3S)-2-benzyl-3-benzyloxycarbonylamino-3-isobutylbutanoate Following the procedure in Example 58, Step 1 and making non critical variations, but starting with benzyl bromide, the title compound is obtained.

Step 2

Preparation of (2S,3S)-2-benzyl-3-benzyloxycarbonylamino-3-isobutylbutyric acid

Following the procedure in Example 58, Step 2 and making non critical variations, but starting with the product of Step 1, the title compound is obtained.

Step 3

Preparation of (R*,S*)-[1-[2-[(4,5-dihydro-5-thioxo-1,3,4-thiadiazol-2-yl)-amino]-2-oxo-1-(phenylmethyl)ethyl]-3-methylbutyl]carbamic acid phenylmethyl ester Following the general procedure outlined in method B, and making noncritical variations, but starting with the product of Step 2, the title compound is obtained.

$^1$H NMR (DMSO) δ: 0.817–0.83, 1.30–1.39, 1.50–1.62, 2.80–2.92, 3.80–3.90, 4.93–5.08, 7.02–7.31, 12.3, 14.1.

MS (EI): m/z: 484, 377, 352, 334, 264, 220, 91, 86.

Preparation of Compounds of Formula VI

EXAMPLE 57

Preparation of ethyl α-[[(4,5-dihydro-5-thioxo-1,3,4-thiadiazol-2yl)amino]carbonyl]benzenepropanoate

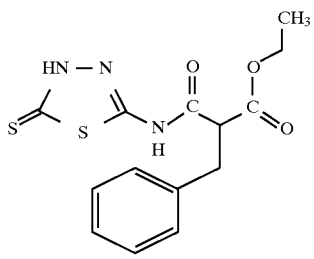

To a cold (0° C.), well stirred, solution of benzyl malonic acid monoethyl ester (1.33 g, 6.0 mmol) in THF (50 mL) is added carbonyldiimidazole (1.05 g, 6.5 mmol) and the reaction is allowed to warm room temperature. After 4 hours, 5-amino-(3H)-1,3,4,-thiadiazole-2-thione (864 mg, 6.5 mmol) is added and stirring continued for 4 days. The reaction mixture is poured into pH 4 buffer, extracted with methylene chloride, and the organic layers combined, dried (anhydrous sodium sulfate) and concentrated. Chromatography of the residue on silica gel (elution with 5% methanol/methylene chloride) gave the title compound as an amorphous solid.

$^1$H NMR (DMSO-d$_6$) δ 7.28–7.21, 4.09, 3.14, 1.12;

IR (mull) 3161, 3026, 1730, 1699, 1575, 1495, 1352, 1302, 1224, 1147, 1068, 1030,774,751, 700 cm$^{-1}$;

MS (EI) m/z 338, 337, 159, 135, 134, 133, 131, 103, 91, 76.

EXAMPLE 58

Preparation of ethyl α-[[(4,5-dihydro-5-thioxo-1,3,4-thiadiazol-2-yl)amino]carbonyl]-3,3-dimethylbutanoate

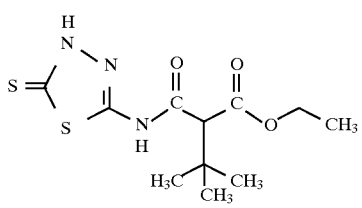

To a solution of tert-butylmalonic acid monoethyl ester (3.0 g, 16.0 mmol) in THF (100 mL) is added carbonyldiimidazole (2.85 g, 17.6 mmol) and the reaction is stirred overnight. 5-Amino-(3H)-1,3,4-thiadiazole-2-thione (864 mg, 6.5 mmol) is added and stirring continued for an additional 72 hours. The reaction mixture is 35 poured into pH 4 buffer, extracted with methylene chloride, and the organic layers combined, dried (anhydrous sodium sulfate) and concentrated. Chromatography of the residue on silica gel (elution with 5% methanol/methylene chloride) gave 1.2 g (25%) of the title compound as an amorphous solid.

$^1$H NMR (DMSO-d$_6$) δ 14.12, 12.56, 4.08, 3.47, 1.14, 1.03;

¹³C NMR (CDCl₃) ppm 184.20, 167.60, 167.52, 151.96, 61.17, 60.28, 34.32, 28.15 (3C), 14.44;

IR (mull) 3255, 3084, 3051, 1709, 1686, 1562, 1332, 1308, 1224, 1177, 1155, 1078, 1073, 1049, 617 cm⁻¹;

MS (EI) m/z 303, 303, 289, 135, 134, 133, 115, 101, 87, 69, 57.

EXAMPLE 59

Preparation of N-methyl-α-[[(4,5-dihydro-5-thioxo-1,3,4-thiadiazol-2-yl)amino]carbonyl]-3,3-dimethylbutanamide

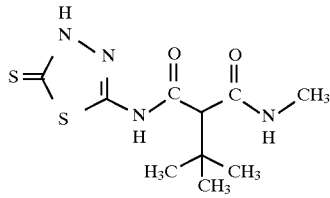

Methanol (10 mL) is saturated with methylamine at 0° C. and ethyl 60 -[[(4,5-dihydro-5-thioxo-1,3,4-thiadiazol-2-yl)amino]carbonyl]-3,3-dimethylbutanoate (500 mg, 1.65 mmol) added. The reaction mixture is allowed to warm to room temperature and stirred overnight. The solvent is removed in vacuo and the residue chromatographed on silica gel (elution with 10% methanol/methylene chloride) to give 325 mg (72%) of the title compound as an amorphous white solid.

¹H NMR (DMSO-d₆) δ 6 14.10, 12.15, 7.85, 3.17, 2.61, 0.99;

¹³C NMR (CDCl₃) ppm 184.22, 169.04, 168.25, 151.60, 61.51, 35.00, 28.52 (3C), 26.38;

IR (mull) 3168, 3097, 1683, 1670, 1640, 1559, 1414, 1400, 1301, 1252, 1192, 1061, 815, 736, 619 cm⁻¹;

MS (EI) m/z 288, 289, 288, 156, 133, 100, 83, 69, 58, 57, 55.

EXAMPLE 60

Preparation of cis-N'-(4,5-dihydro-5-thioxo-1,3,4-thiadiazol-2-yl)-N-(phenylmethoxy)-N-(phenylmethyl)-1,3-cyclopentane dicarboxamide

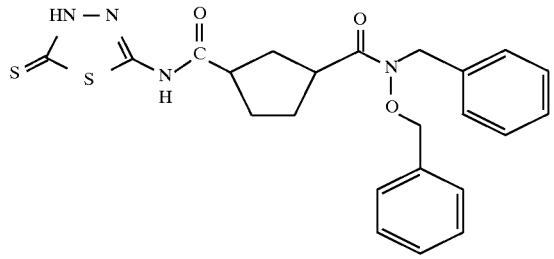

Step 1

Preparation of cis-3-[[(Phenylmethoxy)(phenylmethyl)amino]carbonyl]-cyclopentane carboxylic acid 552 mg of 3-Oxabicyclo[3.2.1]octane-2,4-dione (3.94 mmol, prepared according to the procedure described in *Chem. Lett.*, p 93, (1994)) is added to a rapidly stirring solution of triethylamine (0.55 mL, 3.94 mmol) and N-benzyl-O-benzylhydroxylamine hydrochloride (983 mg, 3.94 mmol) in CH₂Cl₂ in a flame dried flask under nitrogen. After stirring at ambient temperature for 3 days, the reaction is quenched with aqueous citric acid (1M). Extraction into CH₂Cl₂ (3×50 mL), followed by drying over MgSO₄, yielded a pale yellow oil, 1.51 g. Recrystallization in ethyl acetate/hexane provided the product as a white crystalline solid, 1.32 g (95%). mp. 118°–120° C.

¹H NMR (CDCl₃) δ 1.77–2.13, 2.89, 3.24, 4.79, 4.83, 7.25–7.38;

¹³C NMR (CDCl₃) ppm 29.6, 30.4, 32.5, 41.1, 44.5, 50.2, 77.0, 127.9, 128.5, 128.7, 128.8, 129.1, 134.1, 136.1, 179.0;

IR (mull) 3034, 3013, 2494, 1996, 1977, 1950, 1730, 1612, 1412, 1208, 1169, 913, 759, 729, 706;

MS (EI) m/z 353 (M+), 231, 213, 180, 141, 113, 95, 92, 91, 67, 65.

Step 2

Preparation of cis-N'-(4,5-dihydro-5-thioxo-1,3,4-thiadiazol-2-yl)-N-(phenylmethoxy)-N-(phenylmethyl)-1,3-cyclopentane dicarboxamide Following the general procedure outline in A and making non critical variations but starting with the product of Step 1 (2.0 g, 5.66 mmol), the title compound is obtained.

¹H NMR (DMSO-d₆) δ 1.75–2.09, 3.21, 3.35, 4.86, 4.92, 7.26–7.39, 12.39, 14.06;

¹³C NMR (DMSO-d₆) ppm 28.9, 29.1, 33.0, 43.9, 47.9, 75.4, 127.2, 127.8, 128.3, 128.4, 128.6, 129.3, 134.6, 136.9, 152.2, 174.1, 175.3, 183.5;

IR (mull) 3282, 3063, 3031, 2340, 1957, 1671, 1617, 1581, 1570, 1488, 1314, 1303, 1065, 758, 697 cm⁻¹;

MS (FAB) m/z 469 (M+H), 577, 546, 545, 470, 469, 468, 368, 336, 256, 91.

SCHEME I
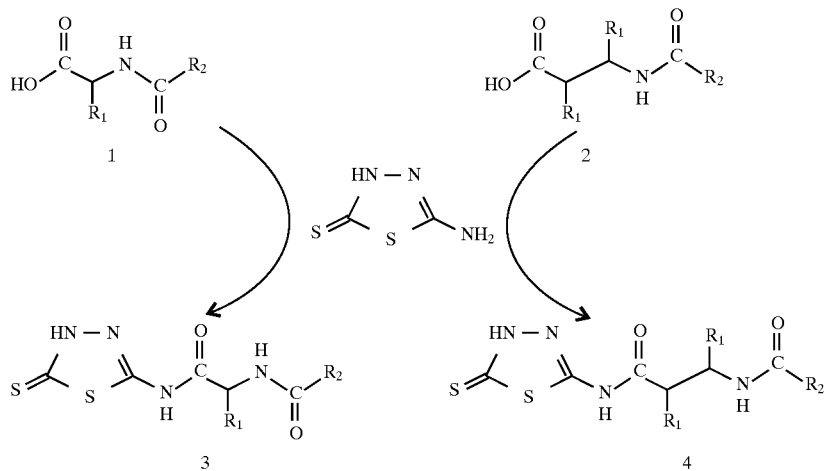
SCHEME IIA
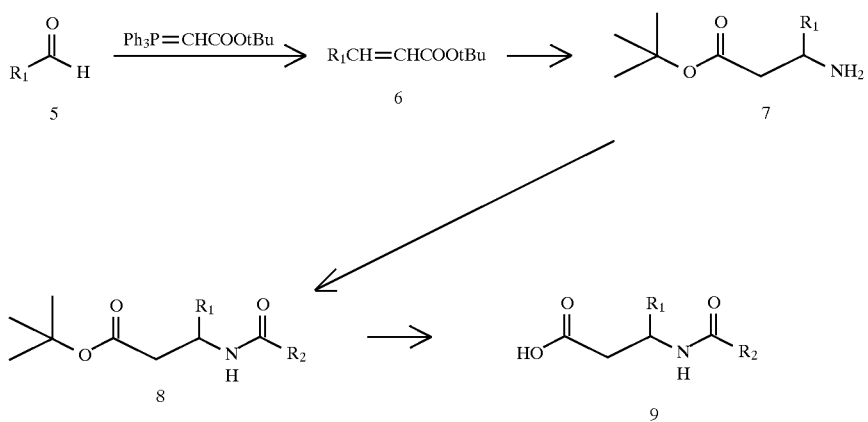
SCHEME IIB
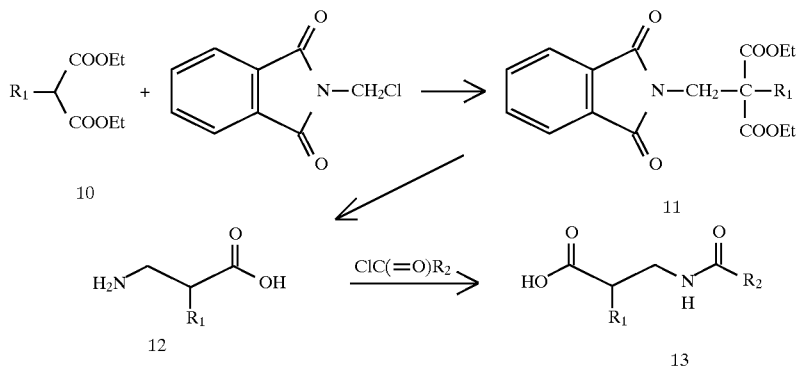

We claim:
1. A compound of a formula I

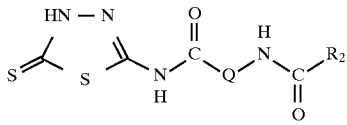    I or pharmaceutical acceptable salts thereof wherein:
Q is

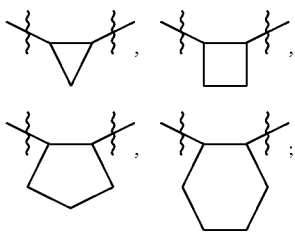    a) b)

$R_1$ is
 a) H,
 b) $C_{2-8}$ alkyl,
 c) phenyl,
 d) $C_{1-8}$ alkyl aryl,
 e) —$(CH_2)_i$—X—$(CH_2)_j$-aryl,
 f) —$(CH_2)_i$—Het,
 g) $C_{3-6}$ alkylene,
 h) $C_{3-6}$ alkylene aryl,
 i) —$(CH_2)_j$-cycloalkyl,
 j) —$C(CH_3)_2$—S—$CH_2$—$NHC(=O)R_3$, or
 k) —$(CH_2)_i$—$NHC(=O)OR_3$;
$R_2$ is
 a) $C_{1-6}$ alkyl,
 b) —$(CH_2)_j$-aryl,
 c) —$(CH_2)_i$-indol-3-yl,
 d) 9H-fluoren-9-ylmethoxy,
 e) —$(CH_2)_j$—$OR_3$, or

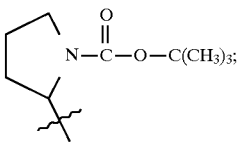

$R_3$ is
 b) a) $C_{1-6}$ alkyl, or
 b) —$(CH_2)_j$-aryl;
X is
 a) S, or
 b) O;
aryl is
 phenyl, optionally substituted with one to five of the following:
  a) halogen,
  b) —$NHC(=O)OR_3$,
  c) —$NO_2$, or
  d) —$CF_3$;
Het is
 a 5-, 6-, 9-, or 10-membered heteroaromatic moiety having one or more atoms selected from the group consisting of N, O, and S;

i is, 1, 2, 3, or 4;
j is 0, 1, 2, 3, or 4;
n is 1 or 2; and
with the following provisos:
 a) when n is 1, and $R_1$ is phenylmethoxymethyl, or benzyl, $R_2$ is other than tert-butyoxy,
 b) when n is 1, $R_1$ is isopropyl, and $R_2$ is tert-butyoxy, the compound is (S) enantiomer,
 c) when n is 1, $R_1$ is phenylmethyl, and $R_2$ is phenylmethoxy, the compound is (S) enantiomer,
 d) when n is 1, $R_1$ is indol-3-methyl, and $R_2$ is phenylmethoxy, the compound is (S) enantiomer, or
 e) when n is 2, at least one $R_1$ is other than hydrogen.

2. A compound of formula I according to claim 1 which is a structure having a formula II

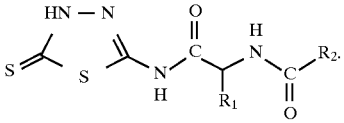    II

3. A compound of formula I according to claim 1 which is a structure having formula III

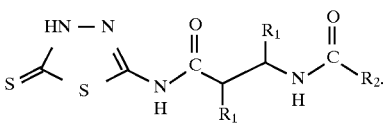    III

4. A compound of formula II according to claim 2 which is an optically pure enantiomer having formula IV

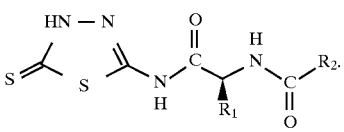    IV

5. A compound of formula II according to claim 3 which is an optically pure enantiomer having formula V

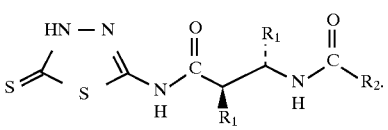    V

6. A compound of claim 1 wherein $R_1$ is hydrogen, phenyl, phenylmethyl, phenylpropyl, (pentafluorophenyl)methyl, n-butyl, isobutyl, sec-butyl, tert-butyl, propyl, isopropyl, 2-methyl-2-butyl, 2-methyl-3-butene-yl, heptyl, cyclohexyl, cyclohexylmethyl, indol-3-ylmethyl, phenylmethoxy methyl, phenylmethylthiomethyl, 2[((acetylamido)methyl)thio]-2-propyl, 2-methyl-4-phenyl-2-butyl, 2-methyl-4-phenyl-3-buten-2-yl, 2-methyl-5-phenyl-3-penten-2-yl, 2-methyl-5-phenyl-2-pentyl, 4-(carbamic acid phenylmethyl ester)phenylmethyl, or 3-(carbamic acid phenylmethyl ester)-1-propyl.

7. A compound of claim 1 wherein $R_2$ is phenyl, phenylmethyl, methoxymethyl, phenylmethoxy, 9H-fluoren-9-ylmethoxy, tert-butyoxy, methyl, 1-phenylethyl, 1-phenybutyl, phenylmethoxymethyl, phenoxymethyl, 1-(2,3,4,5,6-pentafluorophenyl)-2-ethyl, 1-[(1,1-dimethylethoxy)carbonyl]-L-prolyl, or 1H-indol-3-ylmethyl.

8. A compound of claim 2 which is
(1) [2-[(4,5-dihydro-5-thioxo-1,3,4-thiadiazol-2-yl)amino]-2-oxo-1-(phenyl)ethyl]carbamic acid, phenylmethyl ester, (2) (S)-[1-[[(4,5-dihydro-5-thioxo-1,3,4-thiadiazol-2-yl)amino]carbonyl]-3-phenylpropyl]carbamic acid phenylmethyl ester, (3) [S-(R*,R*)]-[1-[[(4,5-dihydro-5-thioxo-1,3,4-thiadiazol-2-yl)amino]carbonyl]-2-methylbutyl]carbamic acid phenylmethyl ester, (4) [S-(R*,R*)]-[1-[[(4,5-dihydro-5-thioxo-1,3,4-thiadiazol-2-yl)amino]carbonyl]-2-methylbutyl]carbamic acid 9H-fluoren-9-yl-methyl ester, (5) [1-[[(4,5-dihydro-5-thioxo-1,3,4-thiadiazol-2-yl)amino]carbonyl]pentyl]carbamic acid phenylmethyl ester, (6) (S)-[1-[[(4,5-dihydro-5-thioxo-1,3,4-thiadiazol-2-yl)amino]carbonyl]-2,2-dimethylpropyl]carbamic acid phenylmethyl ester, (7) (S)-[1-[[(4,5-dihydro-5-thioxo-1,3,4-thiadiazol-2-yl)amino]carbonyl]butyl]-carbamic acid phenylmethyl ester, (8) [2-[(4,5-dihydro-5-thioxo-1,3,4-thiadiazol-2-yl)amino]-2-oxo-1-[(phenylmethoxy)methyl]ethyl]carbamic acid phenylmethyl ester, (9) [2-[(4,5-dihydro-5-thioxo-1,3,4-thiadiazol-2-yl)amino]-2-oxo-1-[[(phenylmethyl)thio]methyl]ethyl]carbamic acid phenylmethyl ester,

(10) [1-[[(4,5-dihydro-5-thioxo-1,3,4-thiadiazol-2-yl)amino]carbonyl]octyl]carbamic acid phenylmethyl ester,

(11) (S)-[1-(cyclohexylmethyl)-2-[(4,5-dihydro-5-thioxo-1,3,4-thiadiazol-2-yl)amino]-2-oxoethyl]carbamic acid phenylmethyl ester,

(12) (S)-[1-(cyclohexyl)-2-[(4,5-dihydro-5-thioxo-1,3,4-thiadiazol-2-yl)amino]-2-oxoethyl]carbamic acid phenylmethyl ester,

(13) α-(acetylamino)-N-(4,5-dihydro-5-thioxo-1,3,4-thiadiazol-2-yl)benzeneacetamide,

(14) N-[2-[(4,5-dihydro-5-thioxo-1,3,4-thiadiazol-2-yl)amino]-2-oxo-1-phenylethyl]benzenepropanamide,

(15) N-[2-[(4,5-dihydro-5-thioxo-1,3,4-thiadiazol-2-yl)amino]-2-oxo-1-phenylethyl]benzenepentanamide,

(16) N-(4,5-dihydro-5-thioxo-1,3,4-thiadiazol-2-yl)-a-[[(phenylmethoxy)acetyl]-amino]benzeneacetamide,

(17) (2-(((acetylamino)methyl)thio)-1-(((4,5-dihydro-5-thioxo-1,3,4-thiadiazol-2-yl)amino)carbonyl)-2-methylpropyl)carbamic acid phenylmethyl ester,

(18) (Z)-(1-(((4,5-dihydro-5-thioxo-1,3,4-thiadiazol-2-yl)amino)carbonyl)-2,2-dimethyl-4-phenyl-3-butenyl)carbamic acid 1,1-dimethylethyl ester,

(19) (1-(((4,5-dihydro-5-thioxo-1,3,4-thiadiazol-2-yl)amino)carbonyl)-2,2-dimethyl-4-phenylbutyl)carbamic acid 1,1-dimethylethyl ester,

(20) (E)-(1-(((4,5-dihydro-5-thioxo-1,3,4-thiadiazol-2-yl)amino)carbonyl)-2,2-dimethyl-5-phenyl-3-pentenyl)carbamic acid 1,1-dimethylethyl ester,

(21) (1-(((4,5-dihydro-5-thioxo-1,3,4-thiadiazol-2-yl)amino)carbonyl)-2,2-dimethyl-5-phenylpentyl)carbamic acid 1,1-dimethylethyl ester,

(22) (1-(((4,5-dihydro-5-thioxo-1,3,4-thiadiazol-2-yl)amino)carbonyl)-2,2-dimethyl-3-butenyl)carbamic acid 1,1-dimethylethyl ester,

(23) (1-(((4,5-dihydro-5-thioxo-1,3,4-thiadiazol-2-yl)amino)carbonyl)-2,2-dimethylbutyl)carbamic acid 1,1-dimethylethyl ester,

(24) [2-[(4,5-dihydro-5-thioxo-1,3,4-thiadiazol-2-yl)amino]-2-oxo-1-phenylethyl]carbamic acid 1,1-dimethylethyl ester,

(25) (S)-[4-[3-[(4,5-dihydro-5-thioxo-1,3,4-thiadiazol-2-yl)amino]-2-[[(1,1-dimethylethoxy)carbonyl]amino]-3-oxopropyl]phenyl]carbamic acid phenylmethyl ester,

(26) (S)-N-[1-[[(4,5-dihydro-5-thioxo-1,3,4-thiadiazol-2-yl)aminocarbonyl]-2,2-dimethylpropyl]benzenepropanamide,

(27) (S)-N-[1-[[(4,5-dihydro-5-thioxo-1,3,4-thiadiazol-2-yl)aminocarbonyl]-2,2-dimethylpropyl]-2,3,4,5,6-pentafluorobenzenepropanamide,

(28) (S)-[2-[(4,5-dihydro-5-thioxo-1,3,4-thiadiazol-2-yl)amino]-2-oxo-1-[(pentafluorophenyl)methyl]ethyl]carbamic acid 1,1-dimethylethyl ester,

(29) 1-[(1,1-dimethylethoxy)carbonyl]-L-prolyl-N-(4,5-dihydro-5-thioxo-1,3,4-thiadiazol-2-yl)-3-methyl-L-valinamide,

(30) Preparation of (S)-α-N-(4,5-dihydro-5-thioxo-1,3,4-thiadiazol-2-yl)-2,3,4,5,6-pentafluoro-[(1-oxo-3-phenylpropyl)amino]benzenepropanamide,

(31) (S)-[1-[[(4,5-dihydro-5-thioxo-1,3,4-thiadiazol-2-yl)amino]carbonyl]-1,4-butanediyl]biscarbamic acid bis (phenylmethyl) ester,

(32) (S)-N-[1-[[(4,5-dihydro-5-thioxo-1,3,4-thiadiazol-2-yl)amino]carbonyl]-2,2-dimethylpropyl]-1H-indole-3-acetamide,

(33) (S)-[2-[(4,5-dihydro-5-thioxo-1,3,4-thiadiazol-2-yl)amino]-1-(1H-indol-3-ylmethyl)-2-oxoethyl]carbamic acid, phenylmethyl ester,

(34) (S)-[2-[(4,5-dihydro-5-thioxo-1,3,4-thiadiazol-2-yl)amino]-2-oxo-1-(phenylmethyl)ethyl]carbamic acid phenylmethyl ester,

(35) (S)-[[(4,5-dihydro-5-thioxo-1,3,4-thiadiazol-2-yl)amino]carbonyl]-3-methylbutyl]carbamic acid phenylmethyl ester,

(36) (S)-[1-[[(4,5-dihydro-5-thioxo-1,3,4-thiadiazol-2-yl)amino]carbonyl]-2-methylpropyl]carbamic acid phenylmethyl ester, or

(37) (S)-[1-[[(4,5-dihydro-5-thioxo-1,3,4-thiadiazol-2-yl)amino]carbonyl]-2,2-dimethylpropyl]carbamic acid 9H-fluoren-9-yl-methyl ester.

9. A compound of claim 3 which is (1) [3-[(4,5-dihydro-5-thioxo-1,3,4-thiadiazol-2-yl)amino]-3-oxo-2-phenylpropyl]carbamic acid phenylmethyl ester, (2) [3-[(4,5-dihydro-5-thioxo-1,3,4-thiadiazol-2-yl)amino]-3-oxo-2-(phenylmethyl)propyl]carbamic acid phenylmethyl ester, (3) [3-[(4,5-dihydro-5-thioxo-1,3,4-thiadiazol-2-yl)amino]-3-oxo-1-(1,1-dimethylethyl)propyl]carbamic acid phenylmethyl ester, (4) [3-[(4,5-dihydro-5-thioxo-1,3,4-thiadiazol-2-yl)amino]-3-oxo-1-phenylpropyl]carbamic acid phenylmethyl ester, (5) α-(benzoylamino)-N-(4,5-dihydro-5-thioxo-1,3,4-thiadiazol-2-yl)benzenepropanamide, (6) N-(4,5-dihydro-5-thioxo-1,3,4-thiadiazol-2-yl)-β-[(phenylacetyl)amino]benzenepropanamide, (7) N-(4,5-dihydro-5-thioxo-1,3,4-thiadiazol-2-yl)-β-[(phenyloxyacetyl)amino]benzenepropanamide, (8) [3-[(4,5-dihydro-5-thioxo-1,3,4-thiadiazol-2-yl)amino]-3-oxo-1-phenylpropyl]-carbamic acid 1,1-dimethylethyl ester, (9) [3-[(4,5-dihydro-5-thioxo-1,3,4-thiadiazol-2-yl)amino]-3-oxo-1-phenylpropyl]-carbamic acid 9H-fluoren-9-yl methyl ester,

(10) N-(4,5-dihydro-5-thioxo-1,3,4-thiadiazol-2-yl)-β [(methoxyacetyl)amino]benzenepropanamide,

(11) N-(4,5-dihydro-5-thioxo-1,3,4-thiadiazol-2-yl)-β [(phenylmethoxyacetyl)amino]benzenepropanamide,

(12) (S)-[3-[(4,5-dihydro-5-thioxo-1,3,4-thiadiazol-2-yl)amino]-3-oxo-1-phenylpropyl]carbamic acid phenylmethyl ester,

(13) (R)-[3-[(4,5-dihydro-5-thioxo-1,3,4-thiadiazol-2-yl)amino]-3-oxo-1-phenylpropyl]carbamic acid phenylmethyl ester,

(14) (S)-[1-[2-[[(4,5-dihydro-5-thioxo-1,3,4-thiadiazol-2-yl)]amino]-2-oxoethyl]-3-methylbutyl]carbamic acid phenylmethyl ester,

(15) (R*,S*)-[2-[[(4,5-dihydro-5-thioxo-1,3,4-thiadiazol-2-yl)amino]carbonyl]-1-(2-methylpropyl)-4-pentenyl] carbamic acid phenylmethyl ester, or
(16) (R*,S*)-[1-[2-[(4,5-dihydro-5-thioxo-1,3,4-thiadiazol-2-yl)amino]-2-oxo-1-(phenylmethyl)ethyl]-3-methylbutyl]carbamic acid phenylmethyl.

10. A compound of formula VI

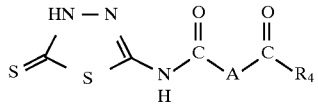
VI or pharmaceutical acceptable salts thereof wherein
A is a) 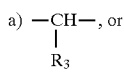 , or b) 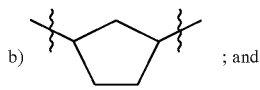 ; and $R_4$ is
   a) —$OCH_2CH_3$,
   b) —$NHCH_3$, or
   c) —$N(CH_2Ph)(OCH_2Ph)$.

11. A method of inhibiting matrix metalloproteinase which comprises administering to a patient in need thereof an effective amount of a compound of claim 1.

12. A method of inhibiting matrix metalloproteinase which comprises administering to a patient in need thereof an effective amount of a compound of claim 10.

13. A method of claim 11 wherein matrix metalloproteinases comprises stromelysins.

14. A method of claim 12 wherein matrix metalloproteinases comprises stromelysins.

15. A method of treating a human, suffering from a disease involving connective tissue degradation, which comprises administering to a patient in need thereof an effective amount of a compound of claim 1.

16. A method of treating a human, suffering from a disease involving connective tissue degradation, which comprises administering to a patient in need thereof an effective amount of a compound of claim 10.

17. A method of claim 15 wherein the disease related to connective tissue degradation is osteoarthrits, rheumatoid arthritis, septic arthritis, osteopenias, osteoporosis, tumor metastasis, periodontitis, gingivitis, corneal ulceration, dermal ulceration, or gastric ulceration.

18. A method of claim 16 wherein the disease related to connective tissue degradation is osteoarthritis, rheumatoid arthritis, septic arthritis, osteopenias, osteoporosis, tumor metastasis, periodontitis, gingivitis, corneal ulceration, dermal ulceration, or gastric ulceration.

19. A pharmaceutical composition which comprises an amount of the compound of claim 1 effective to inhibit matrix metalloproteinase and a pharmaceutically acceptable carrier.

20. A pharmaceutical composition which comprises an amount of the compound of claim 10 effective to inhibit matrix metalloproteinase and a pharmaceutically acceptable carrier.

21. The method of claim 11 wherein the effective amount of the compound of claim 1 is administered orally, parenterally, or topically in a pharmaceutical composition.

22. The method of claim 12 wherein the effective amount of the compound of claim 10 is administered orally, parenterally, or topically in a pharmaceutical composition.

23. The method of claim 15 wherein the effective amount of the compound of claim 1 is administered orally, parenterally, or topically in a pharmaceutical composition.

24. The method of claim 16 wherein the effective amount of the compound of claim 10 is administered orally, parenterally, or topically in a pharmaceutical composition.

25. The method of claim 11 wherein said compound is administered in an amount of from about 0.1 to about 100 mg/kg of body weight/day.

26. The method of claim 12 wherein said compound is administered in an amount of from about 0.1 to about 100 mg/kg of body weight/day.

27. The method of claim 15 wherein said compound is administered in an amount of from about 0.1 to about 100 mg/kg of body weight/day.

28. The method of claim 16 wherein said compound is administered in an amount of from about 0.1 to about 100 mg/kg of body weight/day.

* * * * *